(12) United States Patent
Eissenstat et al.

(10) Patent No.: US 8,048,871 B2
(45) Date of Patent: Nov. 1, 2011

(54) COMPOSITIONS AND METHODS FOR INHIBITING CYTOCHROME P450

(75) Inventors: Michael Eissenstat, Frederick, MD (US); Dehui Duan, Gaithersburg, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 290 days.

(21) Appl. No.: 11/841,157

(22) Filed: Aug. 20, 2007

(65) Prior Publication Data

US 2008/0113945 A1    May 15, 2008

Related U.S. Application Data

(60) Provisional application No. 60/822,860, filed on Aug. 18, 2006.

(51) Int. Cl.
*A61K 31/33* (2006.01)
(52) U.S. Cl. .................................... 514/183
(58) Field of Classification Search .............. 514/183
See application file for complete search history.

(56) References Cited

FOREIGN PATENT DOCUMENTS

WO    WO 2005/087728 A1    9/2005

OTHER PUBLICATIONS

Dorwald, F. 'Side Reactions in Organic Synthesis, A Guide to Successful Synthesis Design' Wiley-VCH, Preface, p. ix, 2005.*
Jordan, V. 'Tamoxifen: a most unlikely pioneering medicine' Nature Reviews, vol. 2, p. 205-213, 2003.*
Cannon, J.G. 'Analog Design' Burger's Medicinal Chemistry and Drug Discovery, Edition 5, vol. 1, Chapter 19, p. 783-802, 1995.*
Horig et al 'From bench to clinic and back: perspective on the 1$^{st}$ IQPC translation research conference' Journal of Translational Medicine, 2(44), p. 1-8, 2004.*
Schafer et al 'Failure is an option: learning from unsuccessful proof-of-concept trials' Drug Discovery Today, 13(21/22), p. 913-916, 2008.*

* cited by examiner

*Primary Examiner* — Brandon Fetterolf
*Assistant Examiner* — Christopher R Stone
(74) *Attorney, Agent, or Firm* — Perkins Coie LLP

(57) ABSTRACT

Methods of inhibiting cytochrome P450 enzymes are provided that can be used for improving the treatment of diseases by preventing degradation of drugs or other molecules by cytochrome P450. Pharmaceutical compositions are provided that can act as boosters to improve the pharmacokinetics, enhance the bioavailability, and enhance the therapeutic effect of drugs that undergo in vivo degradation by cytochrome P450 enzymes.

25 Claims, 27 Drawing Sheets

| COMPOUND | STRUCTURE | Molecular Formula | MW |
|---|---|---|---|
| 1 | 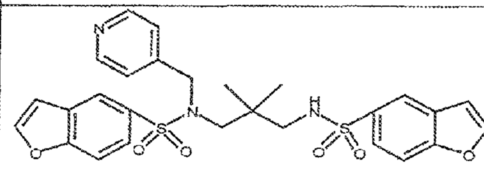 | C27H27N3O6S2 | 553.66 |
| 2 | 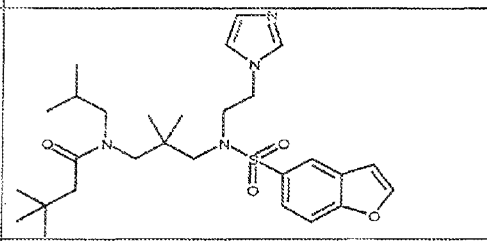 | C28H42N4O4S | 530.73 |
| 3 | 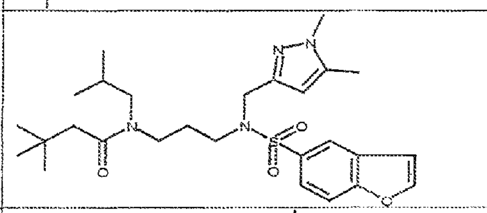 | C27H40N4O4S | 516.70 |
| 4 | 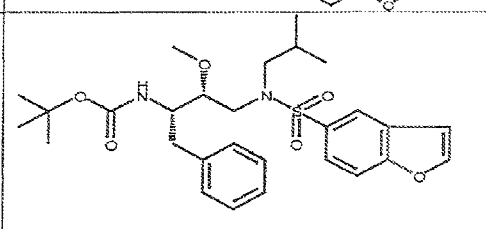 | C28H38N2O6S | 530.68 |
| 5 | 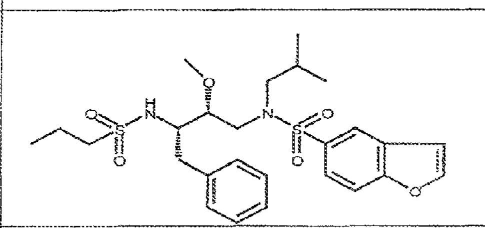 | C26H36N2O6S2 | 536.71 |
| 6 | 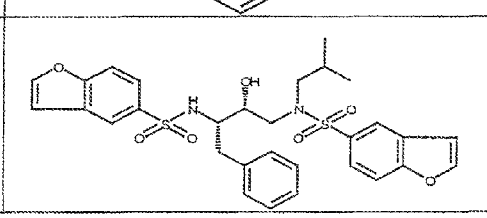 | C30H32N2O7S2 | 596.72 |

FIGURE 1

| 7 |  | C29H31N3O6S2 | 581.71 |
| 8 |  | C27H36N2O5S | 500.66 |
| 9 |  | C33H32N4O6S2 | 644.77 |
| 10 |  | C29H39N3O3 | 477.65 |
| 11 |  | C27H40N4O4S | 516.70 |
| 12 |  | C30H34N2O6S | 550.67 |

| 13 |  | C27H37N3O4S | 499.67 |
| 14 |  | C26H33N3O3 | 435.57 |
| 15 |  | C26H34N2O6S | 502.63 |
| 16 |  | C27H37N3O4S | 499.67 |
| 17 |  | C27H37N3O4S | 499.67 |
| 18 |  | C29H41N3O4S | 527.73 |

| | | | |
|---|---|---|---|
| 19 |  | C30H38N2O8S | 586.70 |
| 20 |  | C26H37N3O4S2 | 519.73 |
| 21 |  | C29H31N3O4 | 485.58 |
| 22 |  | C26H35N3O5S | 501.65 |
| 23 |  | C28H39N3O5S | 529.70 |
| 24 |  | C31H28N4O6S2 | 616.71 |

| 25 |  | C31H39N3O4S | 549.73 |
| 26 |  | C28H31N3O6S3 | 601.76 |
| 27 |  | C26H33N3O4 | 451.57 |
| 28 |  | C27H36N2O6S | 516.66 |
| 29 |  | C30H34N2O6S | 550.67 |
| 30 |  | C29H40N2O5S | 528.71 |

| 31 | | C27H36N2O6S | 516.66 |
|---|---|---|---|
| 32 | | C29H30N6O6S2 | 622.72 |
| 33 | | C28H39N3O4S | 513.70 |
| 34 | | C26H38N4O4S | 502.68 |
| 35 | | C39H32N4O6S2 | 716.83 |
| 36 | | C26H38N4O4S | 502.68 |

FIGURE 1 (continued)

| 37 | | C28H32N4O5S | 536.65 |
|---|---|---|---|
| 38 | | C29H38N4O4S | 538.71 |
| 39 | | C29H25N3O6S2 | 575.66 |
| 40 | | C30H31F3N2O5S | 588.64 |
| 41 | | C28H32N4O6S2 | 584.71 |
| 42 | | C25H37N5O4S | 503.67 |

FIGURE 1 (continued)

| 43 |  | C24H32N2O6S2 | 508.66 |
| --- | --- | --- | --- |
| 44 |  | C27H36N2O6S | 516.66 |
| 45 |  | C24H24N4O6S2 | 528.61 |
| 46 |  | C26H37N3O4S2 | 519.73 |
| 47 |  | C28H39N3O5S | 529.70 |
| 48 |  | C26H37N3O4S2 | 519.73 |

| 49 | | C26H35N3O4S | 485.65 |
|---|---|---|---|
| 50 | | C27H34N4O4S3 | 574.78 |
| 51 | | C29H31N3O4 | 485.58 |
| 52 | | C30H43N3O5S | 557.75 |
| 53 | | C25H38N2O4 | 430.59 |
| 54 | | C28H38N2O6S | 530.68 |

FIGURE 1 (continued)

| | | | |
|---|---|---|---|
| 55 |  | C27H36N2O5S | 500.66 |
| 56 |  | C26H35N3O5S | 501.65 |
| 57 |  | C31H28N4O6S2 | 616.71 |
| 58 |  | C35H36N6O7S2 | 716.84 |
| 59 |  | C28H41N3O4S2 | 547.78 |
| 60 |  | C27H36N2O6S | 516.66 |
| 61 |  | C25H38N2O4 | 430.59 |

| 62 |  | C26H38N4O4S | 502.68 |
| 63 |  | C26H36N4O3 | 452.60 |
| 64 |  | C25H33N3O3S | 455.62 |
| 65 |  | C28H36N2O5 | 480.60 |
| 66 |  | C30H33N3O5 | 515.61 |
| 67 |  | C24H33N3O4S2 | 491.67 |

| 68 |  | C23H29N3O4S | 443.57 |
| 69 |  | C28H35N3O6S | 541.67 |
| 70 |  | C31H36N2O6S | 564.70 |
| 71 |  | C26H34N2O5S | 486.63 |
| 72 |  | C27H37N3O5S | 515.67 |
| 73 |  | C25H30N2O6S2 | 518.65 |
| 74 |  | C32H32N2O5 | 524.62 |

| 75 | | C26H42N2O5S | 494.69 |
|---|---|---|---|
| 76 | | C27H34N2O7S | 530.64 |
| 77 | | C29H41N3O4S | 527.73 |
| 78 | | C28H41N3O4S2 | 547.78 |
| 79 | | C25H36N4O4S | 488.65 |
| 80 | | C29H41N3O4S | 527.73 |

FIGURE 1 (continued)

| | | | |
|---|---|---|---|
| 81 | | C25H34N2O6S2 | 522.68 |
| 82 | | C24H38N2O5S | 466.64 |
| 83 | | C29H38N2O6S2 | 574.76 |
| 84 | | C27H36N2O5S | 500.66 |
| 85 | | C23H36N2O4S | 436.61 |
| 86 | | C29H40N6O4S | 568.74 |
| 87 | | C29H32N2O5S | 520.65 |

FIGURE 1 (continued)

| | | | |
|---|---|---|---|
| 88 |  | C28H37ClN2O6S | 565.13 |
| 89 |  | C25H23N3O6S2 | 525.60 |
| 90 |  | C28H38N2O6S | 530.68 |
| 91 |  | C22H27N3O5S | 445.54 |
| 92 |  | C28H38N2O6S | 530.68 |
| 93 |  | C29H40N2O6S | 544.71 |

| 94 |  | C27H36N2O6S | 516.66 |
| 95 |  | C29H44N4O4S | 544.76 |
| 96 |  | C21H25N3O5S | 431.51 |
| 97 |  | C27H34N2O6S2 | 546.70 |
| 98 |  | C28H37N3O4 | 479.62 |
| 99 |  | C32H41N3O7S2 | 643.82 |

| 100 |  | C28H38N2O6S | 530.68 |
| 101 |  | C26H35N3O5S | 501.65 |
| 102 |  | C23H26N2O6S2 | 490.60 |
| 103 |  | C24H36N2O5S | 464.62 |
| 104 |  | C22H27N3O5S | 445.54 |
| 105 |  | C25H23N3O6S2 | 525.60 |
| 106 |  | C27H40N4O4S | 516.70 |

| 107 |  | C21H32N2O4S | 408.56 |
| 108 |  | C23H30N2O6S2 | 494.63 |
| 109 |  | C27H35N3O3 | 449.59 |
| 110 |  | C27H36N2O5S | 500.66 |
| 111 |  | C23H29N3O4S | 443.57 |
| 112 |  | C31H28N4O6S2 | 616.71 |
| 113 |  | C29H38N2O7S | 558.69 |

| 114 |  | C25H38N2O7S | 510.65 |
| 115 |  | C23H29N3O5S | 459.56 |
| 116 |  | C25H38N2O4 | 430.59 |
| 117 |  | C22H29N3O4S2 | 463.62 |
| 118 |  | C22H29N3O4S2 | 463.62 |
| 119 |  | C25H33N3O4S | 471.62 |
| 120 |  | C27H44N2O4S | 492.72 |

| 121 |  | C23H28N2O5S | 444.55 |
| --- | --- | --- | --- |
| 122 |  | C27H36N2O5S | 500.66 |
| 123 |  | C28H38N2O5S | 514.68 |
| 124 |  | C27H30N4O6S2 | 570.69 |
| 125 |  | C28H41N3O4S2 | 547.78 |
| 126 |  | C22H28N4O4S | 444.55 |

| 127 |  | C30H33ClN2O6S | 585.12 |
| 128 |  | C23H28N2O5S | 444.55 |
| 129 |  | C24H38N2O5S | 466.64 |
| 130 |  | C24H32N2O6S2 | 508.66 |
| 131 |  | C29H28N4O6S4 | 656.82 |
| 132 |  | C28H31N3O4S | 505.64 |
| 133 |  | C37H38N2O6S | 638.78 |

| 134 |  | C23H28N2O5S | 444.55 |
| 135 |  | C22H34N2O6S | 454.59 |
| 136 |  | C28H38N2O6S | 530.68 |
| 137 |  | C27H38N2O6S2 | 550.74 |
| 138 |  | C28H37N3O6S | 543.68 |
| 139 |  | C29H40N6O4S | 568.74 |

| 140 |  | C24H23N3O6S3 | 545.65 |
| 141 |  | C22H27N3O4S | 429.54 |
| 142 |  | C23H36N2O5S | 452.61 |
| 143 |  | C23H36N2O4S | 436.61 |
| 144 |  | C29H40N2O5S | 528.71 |
| 145 |  | C25H23N3O6S2 | 525.60 |

| 146 | | C26H35N3O5S | 501.65 |
|---|---|---|---|
| 147 | | C25H40N2O5S | 480.67 |
| 148 | | C34H42N2O6S | 606.78 |
| 149 | | C23H32N4O4S | 460.60 |
| 150 | | C21H30N2O4 | 374.48 |
| 151 | | C31H38N2O5S | 550.72 |
| 152 | | C27H36N2O6S | 516.66 |

FIGURE 1 (continued)

| 153 | | C22H26N2O5S | 430.52 |
|---|---|---|---|
| 154 | | C24H30N2O5S | 458.58 |
| 155 | | C30H34N2O5S | 534.67 |
| 156 | | C21H32N2O4S | 408.56 |
| 157 | | C27H42N2O5S | 506.71 |
| 158 | | C26H42N2O5S | 494.69 |
| 159 | | C25H25N3O6S2 | 527.62 |

FIGURE 1 (continued)

| | | | |
|---|---|---|---|
| 160 |  | C27H42N2O5S | 506.71 |
| 161 |  | C25H39N3O4 | 445.60 |
| 162 |  | C33H40N2O5S | 576.76 |
| 163 |  | C28H38N2O5S | 514.68 |
| 164 |  | C23H26N2O6S2 | 490.60 |
| 165 |  | C23H34N2O5S | 450.60 |
| 166 |  | C23H27N3O4 | 409.49 |
| 167 |  | C26H42N2O5S | 494.69 |

| 168 |  | C22H34N2O5S | 438.59 |

COMPOSITIONS AND METHODS FOR INHIBITING CYTOCHROME P450

This application claims priority to provisional application Ser. No. 60/822,860, filed Aug. 18, 2006, the contents of which are hereby incorporated by reference in their entirety.

The technology provides methods of inhibiting cytochrome P450 enzymes. The technology also provides methods of enhancing the therapeutic effect of drugs that are metabolized by cytochrome P450 enzymes, methods of decreasing the toxic effects of drugs that are metabolized to toxic by-products by cytochrome P450 enzymes, methods of increasing oral bioavailability of drugs that are metabolized by cytochrome p450 enzymes, and methods of curing diseases that are caused or exacerbated by the activity of cytochrome P450 enzymes.

BACKGROUND OF THE TECHNOLOGY

Cytochrome P450s (P450) are a family of enzymes involved in the oxidative metabolism of both endogenous and exogenous compounds. P450 enzymes are widely distributed in the liver, intestines and other tissues (Krishna et al., *Clinical Pharmacokinetics.* 26:144-160, 1994). P450 enzymes catalyze the phase I reaction of drug metabolism, to generate metabolites for excretion. The classification of P450s is based on homology of the amino acid sequence (Slaughter et al *The Annals of Pharmacotherapy* 29:619-624, 1995). In mammals, there is over 55% homology of the amino acid sequence of CYP450 subfamilies. The differences in amino acid sequence constitute the basis for a classification of the superfamily of cytochrome P450 enzymes into families, subfamilies and isozymes.

Cytochrome P450 contains an iron cation and is a membrane bound enzyme that can carry out electron transfer and energy transfer. Cytochrome P450, when bound to carbon monoxide (CO), displays a maximum absorbance (peak) at 450 nm in the visible spectra, and is therefore called P450 (Omura et al., *J. Biol. Chem.* 239:2370, 1964).

Over 200 genes encoding cytochrome P450s have been identified, and are divided among over 30 gene families. These gene families are organized into subfamilies, which vary in regulation of gene expression and in amino acid sequence homology, substrate specificity, catalytic activity, and physiological role of the encoded enzymes. Representative P450 genes and substrates of the encoded enzymes are discussed below.

Listed below are examples of known substrates of members of various P450 subfamilies. See also the discussion in Klassen, ed., *Casarett and Doull's Toxicology: The Basic Science of Poisons,* McGraw-Hill, 1996, pp. 150 ff. Further information about cytochrome P450 substrates, can be found in Gonzales and other review articles cited above. Current information sources available via the Internet include the "Cytochrome P450 Homepage", maintained by David Nelson, the "Cytochrome P450 Database", provided by the Institute of Biomedical Chemistry & Center for Molecular Design, and the "Directory of P450-containing Systems", provided by Kirill N. Degtyarenko and Peter Fabian.

CYP1A1: diethylstilbestrol, 2- and 4-hydroxyestradiol

CYP1A2: acetaminophen, phenacetin, acetanilide (analgesics), caffeine, clozapine (sedative), cyclobenzaprine (muscle relaxant), estradiol, imipramine (antidepressant), mexillitene (antiarrythmic), naproxen (analgesic), riluzole, tacrine, theophylline (cardiac stimulant, bronchodilator, smooth muscle relaxant), warfarin.

CYP2A6: coumarin, butadiene, nicotine

CYP2A 13: nicotine

CYP2B1: phenobarbital, hexobarbital

CYP2C9: NSAIDs such as diclofenac, ibuprofen, and piroxicam; oral hypoglycemic agents such as tolbutamide and glipizide; angiotensin-2 blockers such as irbesartan, losartan, and valsartan; naproxen (analgesic); phenyloin (anticonvulsant, antiepileptic); sulfamethoxazole, tamoxifen (antineoplastic); torsemide; warfarin, flurbiprofen CYP2C19: hexobarbital, mephobarbital, imipramine, clomipramine, citalopram, cycloguanil, the anti-epileptics phenyloin and diazepam, S-mephenyloin, diphenylhydantoin, lansoprazole, pantoprazole, omeprazole, pentamidine, propranolol, cyclophosphamide, progesterone CYP2D6: antidepressants (imipramine, clomipramine, desimpramine), antipsychotics (haloperidol, perphenazine, risperidone, thioridazine), beta blockers (carvedilol, S-metoprolol, propafenone, timolol), amphetamine, codeine, dextromethorphan, fluoxetine, S-mexiletine, phenacetin, propranolol CYP2E1: acetaminophen; chlorzoxazone (muscle relaxant), ethanol; caffeine, theophylline; dapsone, general anesthetics such as enflurane, halothane, and methoxyflurane; nitrosamines CYP3A4: HIV Protease Inhibitors such as indinavir, ritonavir, lopinavir, amprenavir, tipranavir, darunavir, and saquinavir; HIV integrase inhibitors such as raltegravir, Hepatitis C virus (HCV) protease inhibitors, benzodiazepines such as alprazolam, diazepam, midazolam, and triazolam; immune modulators such as cyclosporine; antihistamines such as astemizole and chlorpheniramine; HMG CoA Reductase inhibitors such as atorvastatin, cerivastatin, lovastatin, and simvastatin; channel blockers such as diltiazem, felodipine, nifedipine, nisoldipine, nitrendipine, and verapamil; antibiotics such as clarithromycin, erythromycin, and rapamycin; various steroids including cortisol, testosterone, progesterone, estradiol, ethinylestradiol, hydrocortisone, prednisone, and prednisolone; acetaminophen, aldrin, alfentanil, amiodarone, astemizole, benzphetamine, budesonide, carbamazepine, cyclophosphamide, ifosfamide, dapsone, digitoxin, quinidine (anti-arrhythmic), etoposide, flutamide, imipramine, lansoprazole, lidocaine, losartan, omeprazole, retinoic acid, FK506 (tacrolimus), tamoxifen, taxol and taxol analogs such as taxotere, teniposide, terfenadine, buspirone, haloperidol (antipsychotic), methadone, sildenafil, trazodone, theophylline, toremifene, troleandomycin, warfarin, zatosetron, zonisamide.

CYP6A1: fatty acids.

The efficacy of a drug can be dramatically affected by its metabolism in the body. For drugs that are rapidly metabolized it can be difficult to maintain an effective therapeutic dose in the body, and the drug often must be given more frequently, in higher dose, and/or be administered in a sustained release formulation. Moreover, in the case of compounds for treating infectious disease, such as viral or bacterial infections, the inability to maintain an effective therapeutic dose can lead to the infectious agent becoming drug resistant. Many compounds that have strong biological efficacy and that would otherwise be potentially powerful therapeutics are rendered essentially useless by virtue of their short half-lives in vivo. A common pathway of metabolism for drugs containing lipophilic moieties is via oxidation by one or more cytochrome P450 enzymes. These enzymes metabolize a drug to a more polar derivative that is more readily excreted through the kidney or liver. First pass metabolism refers to the elimination of drugs via liver and intestinal CYP450 enzymes. First pass metabolism can lead to poor drug absorption from the GI tract due to extensive intestinal CYP450 metabolism, low plasma blood levels due to hepatic CYP450 metabolism, or both. Poor oral bioavailability due to CYP450 metabolism is a major reason for the failure of drugs candidates in clinical trials. In some instances, metabolic by-products of CYP450 enzymes are highly toxic and can result in severe side effects, cancer, and even death.

Some examples of the effects of drug metabolism by CYPs include:

Acetaminophen: Ethanol up-regulates CYP2E1, which metabolizes acetaminophen to a reactive quinone. This reactive quinone intermediate, when produced in sufficient amounts, causes liver damage and necrosis.

Sedatives: The sedative phenobarbital (PB) up-regulates several P450 genes, including those of the CYP2B and CYP3A subfamilies. Upregulation of these enzymes increases the metabolism and reduces the sedative effects of PB and the related sedative hexobarbital.

Antibiotics: The antibiotics rifampicin, rifampin, rifabutin, erythromycin, and related compounds are inducers of the CYP3A4 gene and are substrates of the enzyme product.

Anti-cancer agents: Taxol and taxotere are potent anti-cancer agents. Both drugs are extensively metabolized by CYP3A4 and have poor oral bioavailability. These drugs are only efficacious in parenteral formulations which, due to their poor solubility properties, are highly noxious to patients.

Nicotine: CYP2A6 and 2A13 convert nicotine, a non-toxic component of cigarette smoke, into NNK, a highly potent carcinogen that contributes to lung cancer from smoking.

Oral contraceptive/estrogen replacement therapy: Estrogens and estradiols are the active ingredients in oral contraceptives and in hormonal replacement therapies for postmenopausal women. Women who are also taking antibiotics such as rifampicin or erythromycin, or glucocorticoids such as dexamethasone, or who smoke, risk decreased efficacy of the estrogen/estradiol treatments due to increased metabolism of these compounds by up-regulated CYP3A4 and/or CYP1A2 enzymes.

Dextromethorphan: CYP2D6 metabolizes dextromethrophan to dextrorphan. Individuals who express high levels of CYP2D6 (so-called rapid metabolizers) do not receive therapeutic benefits from dextromethorphan due to extensive first-pass metabolism and rapid systemic clearance.

Protease Inhibitors Protease inhibitors and non-nucleoside reverse transcriptase inhibitors currently indicated for use in treatment of HIV or HCV are typically good substrates of cytochrome P450 enzymes; in particular, they are metabolized by CYP3A4 enzymes (see e.g. Sahai, AIDS 10 Suppl 1:S21-5, 1996) with possible participation by CYP2D6 enzymes (Kumar et al., *J. Pharmacol. Exp. Ther.* 277(1):423-31, 1996). Although protease inhibitors are reported to be inhibitors of CYP3A4, some non-nucleoside reverse transcriptase inhibitors, such as nevirapine and efavirenz, are inducers of CYP3A4 (see e.g. Murphy et al., *Expert Opin Invest Drugs* 5/9: 1183-99, 1996).

Human CYP450 isozymes are widely distributed among tissues and organs (Zhang et al., *Drug Metabolism and Disposition.* 27:804-809, 1999). With the exception of CYP1A1 and CYP2A13, most human CYP450 isozymes are located in the liver, but are expressed at different levels (Waziers J. Pharmacol. Exp. Ther. 253: 387, 1990). A solution to the problem of drug degradation and first-pass metabolism is to control the rate of drug metabolism. When the rates of drug absorption and metabolism reach a steady state, a maintenance dose can be delivered to achieve a desired drug concentration that is required for drug efficacy. Certain natural products have been shown to increase bioavailability of a drug. For example, the effect of grapefruit juice on drug pharmacokinetics is well known. See Edgar et al., Eur. J. Clin. Pharmacol. 42:313, (1992); Lee et al., Clin. Pharmacol. Ther. 59:62, (1996); Kane et al., Mayo Clinic Proc. 75:933, (2000). This effect of grapefruit juice is due to the presence of natural P450-inhibiting components. Other compounds also have been used for inhibition of P450. For example, the HIV-1 protease inhibitor Ritonavir® is now more commonly prescribed for use in combination with other, more effective, HIV protease inhibitors because of its ability to "boost" those other compounds by inhibiting P450-mediated degradation.

Present methods of inhibiting cytochrome P450 enzymes are not wholly satisfactory because of toxicity issues, high cost, and other factors. For example, using ritonavir to inhibit cytochrome P450 is not desirable in disorders other than HIV infection. It is apparent, therefore, that new and improved methods of inhibiting cytochrome P450 enzymes are greatly to be desired. In particular, methods where an inhibitor can be co-administered with another biologically active compound that is metabolized by cytochrome P450 enzymes are highly desirable.

SUMMARY OF THE TECHNOLOGY

The technology provides methods of inhibiting cytochrome P450 enzymes. The technology also provides methods of enhancing the therapeutic effect of drugs that are metabolized by cytochrome P450 enzymes, methods of decreasing the toxic effects of drugs that are metabolized to toxic by-products by cytochrome P450 enzymes, methods of increasing oral bioavailability of drugs that are metabolized by cytochrome P450 enzymes, and methods of curing diseases that are caused or exacerbated by the activity of cytochrome P450 enzymes.

An advantage of the technology is that it provides improved inhibitors of cytochrome P450 enzymes. Another advantage is that it provides a method of controlling the pharmacokinetic properties of drugs. Another advantage is that it helps control the rate of metabolism of drugs. Another advantage is that it controls the degradation of drugs. Another advantage is that it enhances the bioavailability of drugs. Another advantage is that it enhances the efficacy of drugs. Another advantage is that it boosts the efficacy of certain drugs so that the drugs can be administered at a lower concentration or dosage thereby reducing their toxicity. Another advantage is that these properties can lower the overall cost associated with the treatment of disorders.

More particularly, in one aspect, the technology provides a method of inhibiting cytochrome P450 monooxygenase by administering a compound represented by a formula:

X-A-B—X' where:

X is a lipophilic group containing from 1 to 12 carbon atoms optionally containing from 1 to 3 heteroatoms independently selected from the group consisting of O, S, and N, A is selected from the group consisting of a bond, —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, where m is 0-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, $CF_3$, OR, $C_3$-$C_7$ cycloalkyl, $C_5$-$C_7$ cycloalkenyl, R6, OR2, SR2, $N(R2)_2$, OR3, SR3, NR2R3, OR6, SR6, and NR2R6, and where $G_1$ and $G_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

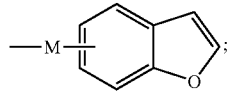

where M is selected from the group consisting of: a bond, $OC(R8)_q$, —CO—, —$SO_n$—, —O—, —O—CO—, —N(D)-$SO_n$—, —N(D)-$CO_n$—, —N(D)-$(R8)_q$-, —$SO_n$—N(D)-$(R8)_q$-, or —$CO_n$—N(D)-$(R8)_q$-, where M can be linked in either orientation with respect to the benzofuran ring, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl, aralkyl, or O-alkyl, where D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, $C(S)R_2$, $C(S)N$ $(R)_2$, $SO_nN(R)_2$, SR, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$, $NRPO_nOR$, oxo, =N—OR, =N—$N(R)_2$, =NR, =NNRC $(O)N(R)_2$, =$NNRCO_nR$, =$NNRS(O)_nN(R)_2$, and =NNRS $(O)_n(R)$;

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$, $NRPO_nOR$;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, $NO_2$, CN, $CO_nR2$, $C(O)N(R2)_2$, $C(O)N(R2)N(R2)_2$, $C(S)R2$, C(S) $N(R2)_2$, $S(O)_nN(R2)_2$, SR2, $SO_nR2$, $N(R)_2$, $N(R2)CO_nR2$, $NR2S(O)_nR2$, NR2C[=N(R2)]$N(R2)_2$, $N(R2)N(R)CO_nR2$, oxo, =N—OR2, =N—$N(R2)_2$, =NR2, =NNRC $(O)N(R2)_2$, =$NNR2C(O)_nR2$, =$NNR2S(O)_nN(R2)_2$, and =$NNR2S(O)_n(R2)$;

R6 is aryl or heteroaryl, where the aryl or heteroaryl optionally are substituted with one or more groups selected from the group consisting of aryl, heteroaryl, R2, R3, halo, OR2, R2OH, R2-halo, $NO_2$, CN, $CO_nR2$, $C(O)N(R2)_2$, C(O) $N(R2)N(R2)_2$, C(S)R2, $C(S)N(R2)_2$, $S(O)_nN(R2)_2$, SR2, $SO_nR2$, $N(R)_2$, $N(R2)CO_nR2$, $NR2S(O)_nR2$, NR2C[=N (R2)]$N(R2)_2$, $N(R2)N(R2)CO_nR2$, OC(O)R2, OC(S)R2, $OC(O)N(R2)_2$, and $OC(S)N(R2)_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, C(S) $N(R)_2$, $SO_nN(R)_2$, SR, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$, $NRPO_nOR$, oxo, =N—OR, =N—$N(R)_2$, =NR, =$NNRC(O)N(R)_2$, =$NNRCO_nR$, =$NNRS(O)_nN$ $(R)_2$, and =$NNRS(O)_n(R)$;

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and q=0-1, where the benzene ring of the benzofuran moiety may optionally by substituted by up to three substituents independently selected from the group consisting of R2, halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, NRS $(O)_nR$, NRC[=N(R)]$N(R)_2$, $N(R)N(R)CO_nR$, $NRPO_n$ $N(R)_2$, and $NRPO_nOR$, where the up to three substituents do not form a ring between any adjacent carbon atoms of the benzene ring, and with the proviso that the compound does not contain a basic aliphatic amine function and does not contain a carboxylic acid group.

In a specific embodiment, there is provided a method of inhibiting cytochrome P450 monooxygenase in a patient by administering to the patient a compound represented by the formula:

X-A-B—X' where:

X is a lipophilic group containing from 1 to 12 carbon atoms optionally containing from 1 to 3 heteroatoms independently selected from the group consisting of O, S, and N, A is —$OCON(R2)$-, —$S(O)_nN(R2)$-, —CON(R2)-, —COCO(NR2)-, —N(R2)CON(R2)-, —$N(R2)S(O)_nN$ (R2)-, N(R2)CO or —N(R2)COO—;

B is —$(CG_1G_2)_m$—, where m is 2-6 and where $G_1$ and $G_2$ are the same or different and where each $G_1$ and $G_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, $CF_3$, OR, $C_3$-$C_7$ cycloalkyl, $C_5$-$C_7$ cycloalkenyl, R6, OR2, SR2, $N(R2)_2$, OR3, SR3, NR2R3, OR6, SR6, and NR2R6, and where $G_1$ and $G_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

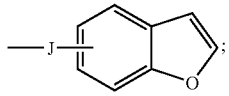

where J is selected from:

—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-, wherein D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, wherein D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, oxo, =N—OR2, =N—N(R2)$_2$, =NR2, =NNRC(O)N(R2)$_2$, =NNR2C(O)$_n$R2, =NNR2S(O)$_n$N(R2)$_2$, and =NNR2S(O)$_n$(R2);

R6 is aryl or heteroaryl, where the aryl or heteroaryl optionally are substituted with one or more groups selected from the group consisting of aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, OC(O)R2, OC(S)R2, OC(O)N(R2)$_2$, and OC(S)N(R2)$_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and where q=0-1.

In another aspect, X may be alkyl, alkenyl, alkynyl, alkoxyalkyl, cycloalkyl, cycloalkylalkyl, heterocycloalkyl, heteroaryl, heterocycloalkylalkyl, aryl, aralkyl, or heteroaralkyl; where X optionally is substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R). In one embodiment, X may be selected from the group consisting of alkyl, cycloalkyl, aryl, aralkyl, heteroaryl, and heteroaralkyl. X optionally is substituted with one or more substituents selected from the group consisting of halo, OR, ROH, R-halo, CN, CO$_n$R, CON(R)$_2$, SO$_n$N(R)$_2$, SR, SO$_n$R, N(R)$_2$, N(R)CO$_n$R, NRS(O)$_n$R, oxo, and =N—OR.

In other aspects, $G_1$ and $G_2$ may be the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl. In specific embodiments, $G_1$ and $G_2$ do not form a ring, or at least one $G_1$ and at least one $G_2$ form a ring. $G_1$ and $G_2$ may be different and, in certain embodiments, neither $G_1$ nor $G_2$ is OH.

In other aspects G1 and G2 are selected from the group consisting of H, O-alkyl, alkyl, optionally substituted aryl and optionally substituted aralkyl.

In the embodiments above, J may be

—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-,.

In the embodiments above, D may be hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, wherein D optionally is substituted by alkyl, halo, nitro, cyano, O-alkyl, or S-alkyl.

In any of the embodiments above, when X is a 5-7 membered non-aromatic monocyclic heterocycle, optionally fused or bridged with one or more 3-7 membered non-aromatic monocyclic heterocycle to form a polycyclic system, wherein any of said heterocyclic ring systems contains one or more heteroatoms selected from O, N, S, and P, and when B is

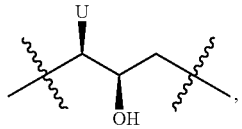

where U is selected from optionally substituted alkyl, optionally substituted alkenyl, optionally substituted alkynyl, optionally substituted aryl, optionally substituted cycloalkyl, or optionally substituted aralkyl, and then J cannot be —N(D)-SO$_n$- or —N(D)-CO$_n$—.

In the methods described above, the cytochrome P450 monoxygenase may be CYP3A4 or CYP3A5.

In other embodiments, the compound used in the methods described above does not inhibit HIV protease.

In specific embodiments, the patient may be suffering from chronic pain, depression, epilepsy, psychosis, inflammation, cancer, cardiovascular disease, diabetes, and/or infection, for example, infection with a hepatitis-causing virus or HIV.

In other embodiments, the compound is administered substantially contemporaneously with a drug where efficacy of the drug is compromised due to degradation by cytochrome P450 monooxygenase.

The details of one or more examples are set forth in the accompanying reaction schemes and description. Further features, aspects, and advantages of the technology will become apparent from the description, the schemes, and the claims.

DETAILED DESCRIPTION

Figure 1:
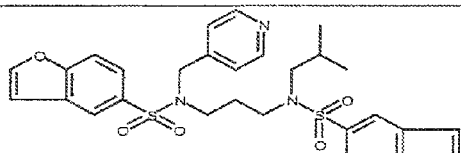
FIG. 1 shows examples of cytochrome P450 inhibitors of the invention. These examples are merely illustrative and not limiting of the present invention.
Figure 1:
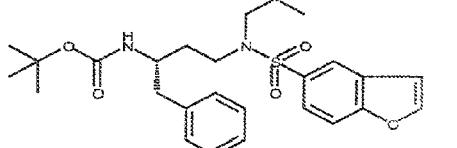
Figure 1:
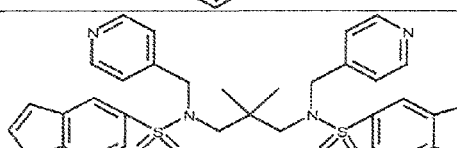
Figure 1:
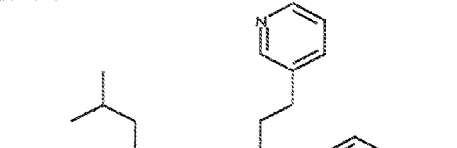
Figure 1:
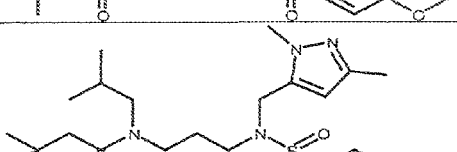
Figure 1:
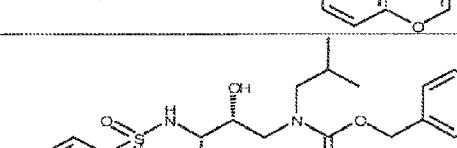
Figure 1:
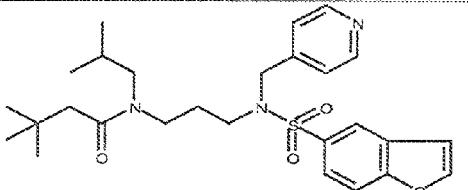
Figure 1:
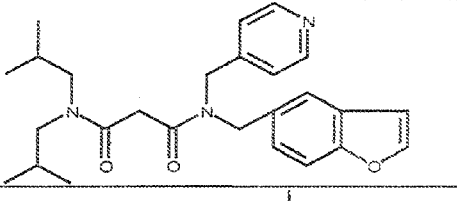
Figure 1:
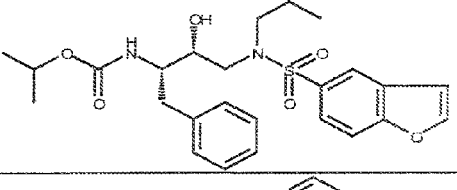
Figure 1:
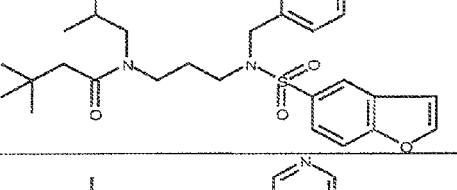
Figure 1:
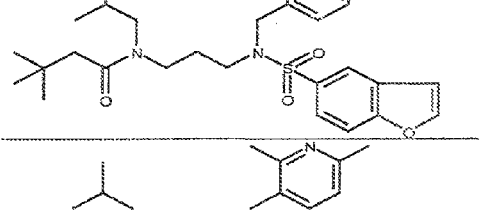
Figure 1:
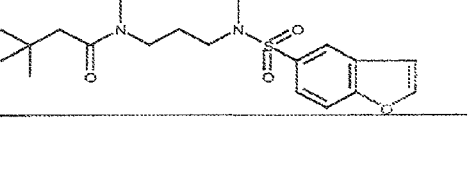
Figure 1:
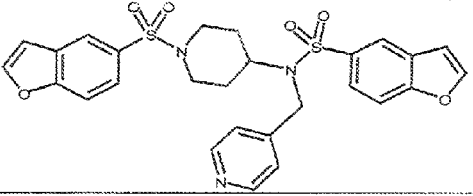
Figure 1:
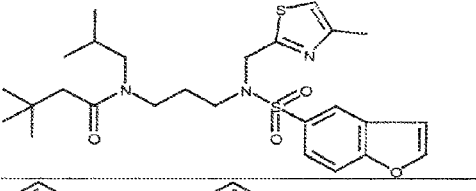
Figure 1:
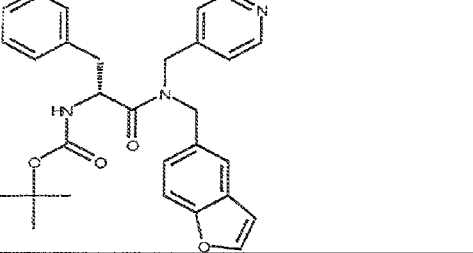
Figure 1:
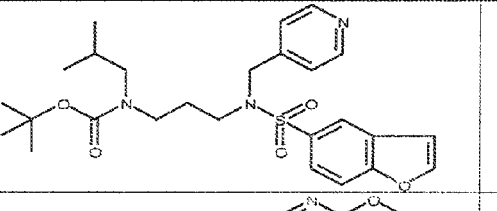
Figure 1:
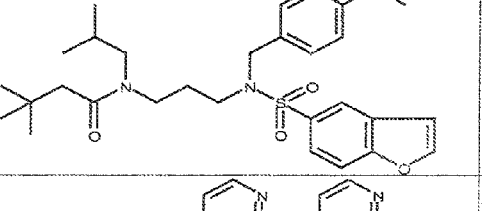
Figure 1:
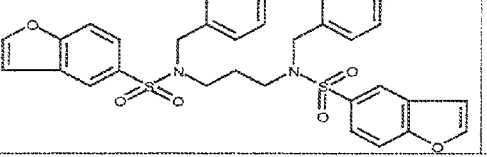
Figure 1:
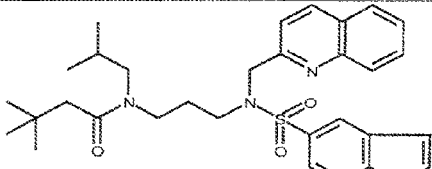
Figure 1:
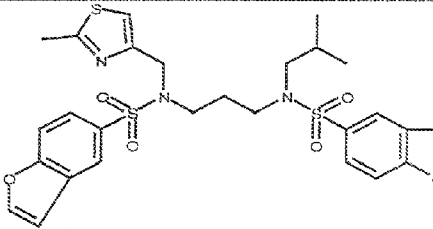
Figure 1:
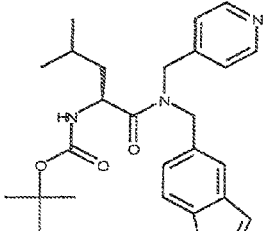
Figure 1:
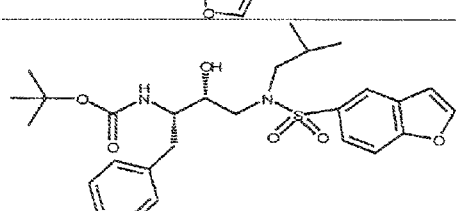
Figure 1:
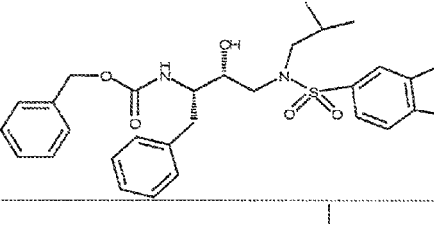
Figure 1:
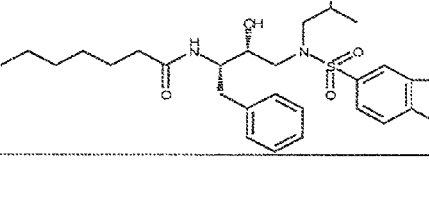
Figure 1:
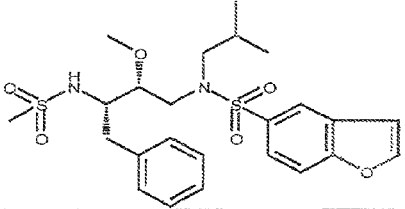
Figure 1:
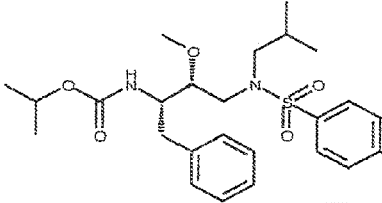
Figure 1:
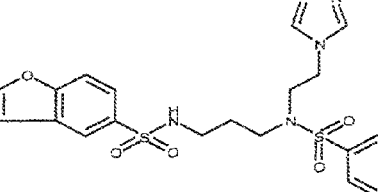
Figure 1:
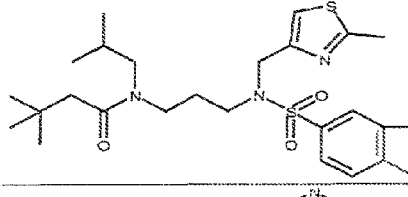
Figure 1:
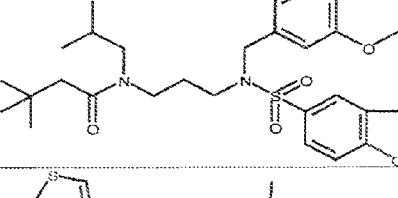
Figure 1:
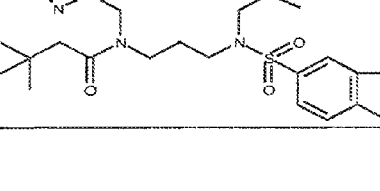
Figure 1:
Figure 1:
Figure 1:
Figure 1:
Figure 1:
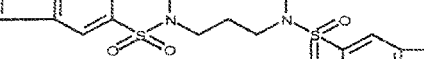
Figure 1:
Figure 1:
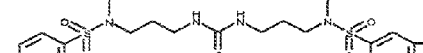
Figure 1:
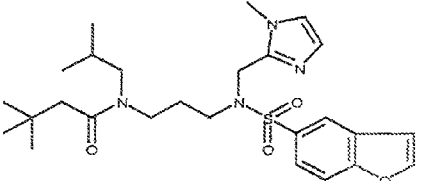
Figure 1:
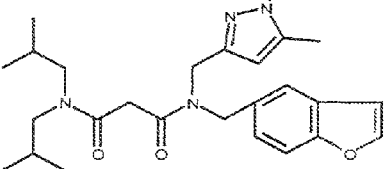
Figure 1:
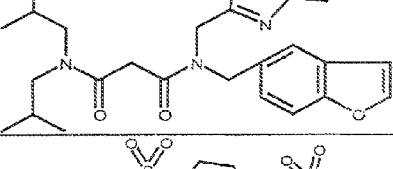
Figure 1:
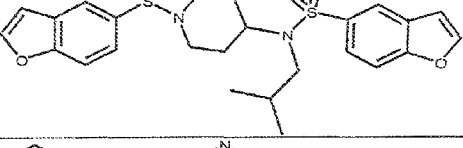
Figure 1:
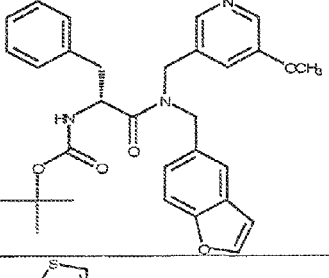
Figure 1:
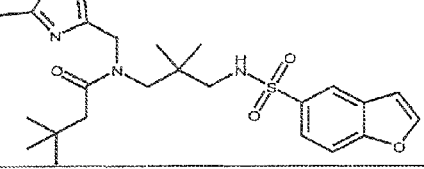
Figure 1:
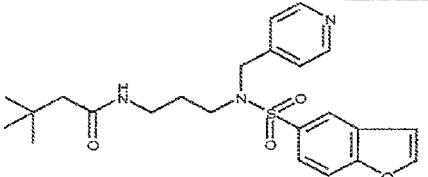
Figure 1:
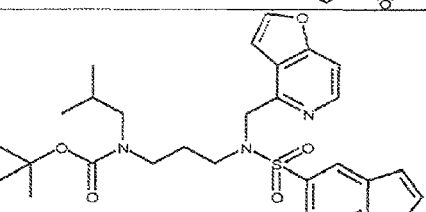
Figure 1:
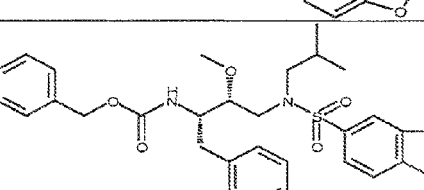
Figure 1:
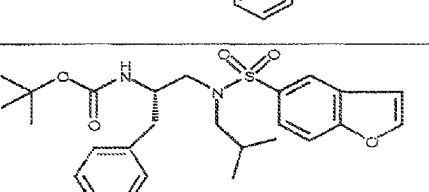
Figure 1:
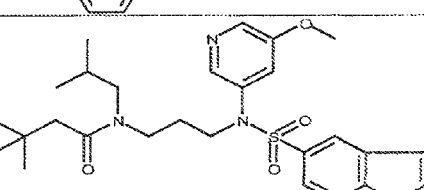
Figure 1:
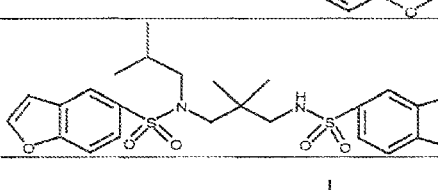
Figure 1:
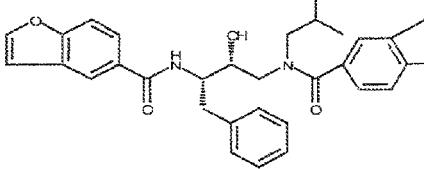
Figure 1:
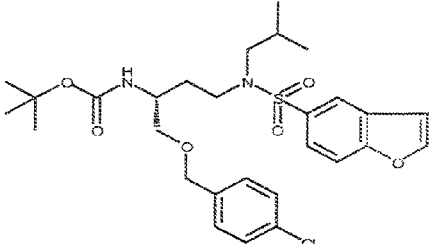
Figure 1:
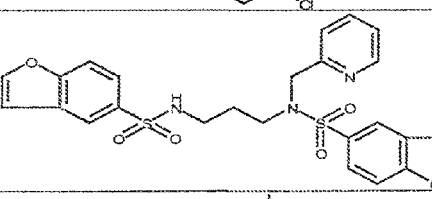
Figure 1:
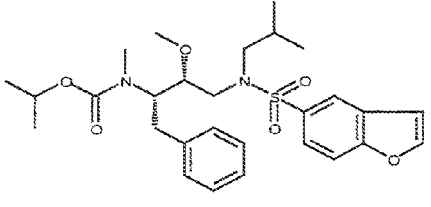
Figure 1:
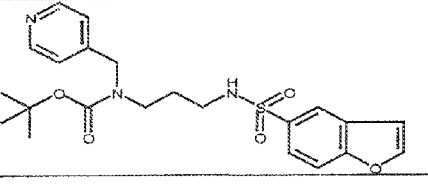
Figure 1:
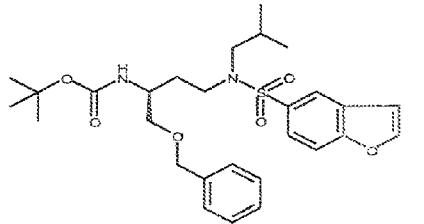
Figure 1:
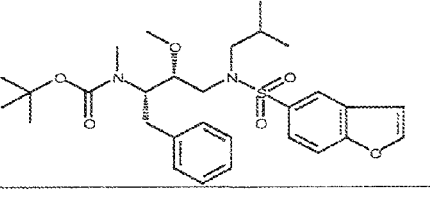
Figure 1:
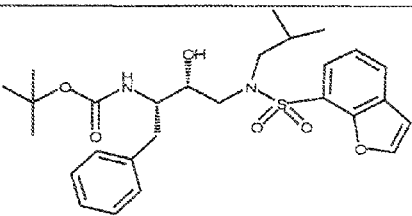
Figure 1:
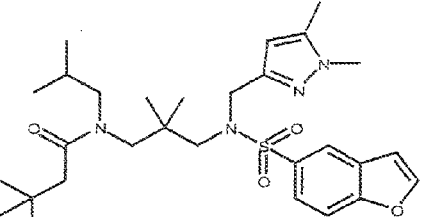
Figure 1:
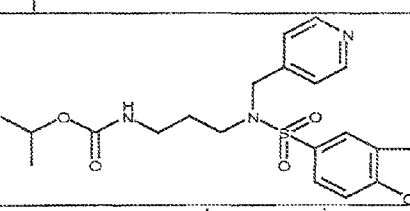
Figure 1:
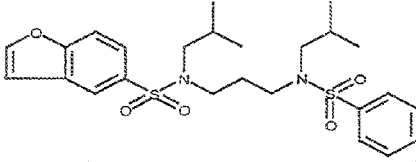
Figure 1:
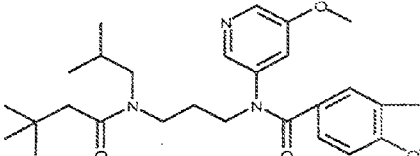
Figure 1:
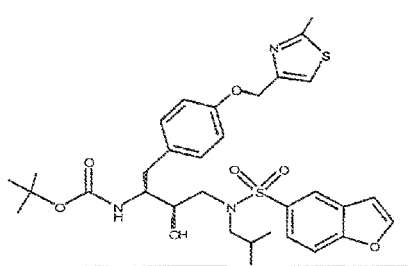
Figure 1:
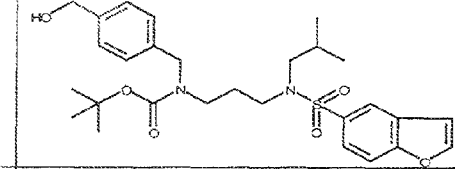
Figure 1:
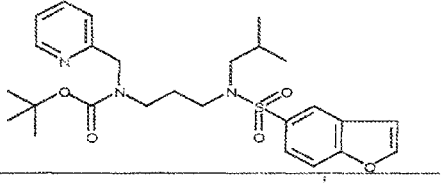
Figure 1:
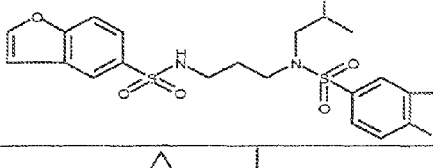
Figure 1:
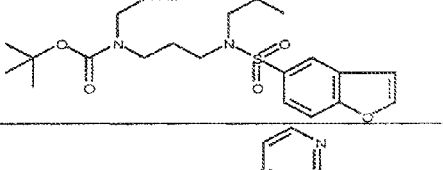
Figure 1:
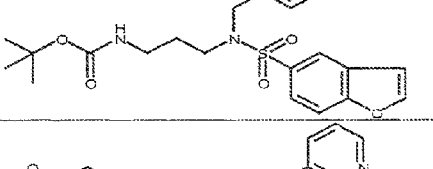
Figure 1:
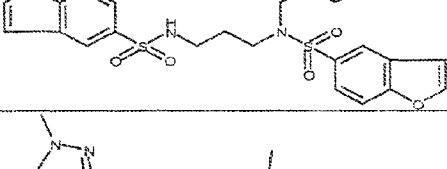
Figure 1:
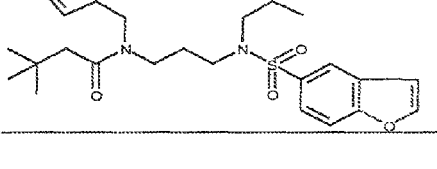
Figure 1:
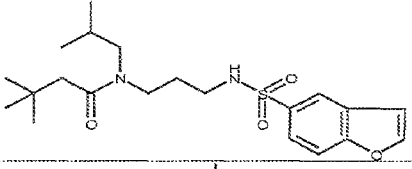
Figure 1:
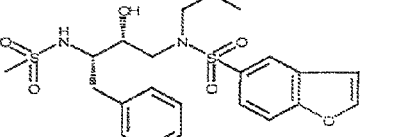
Figure 1:
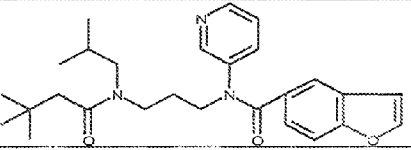
Figure 1:
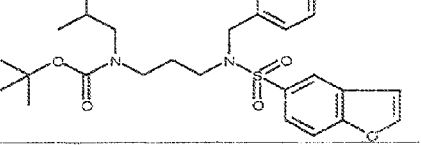
Figure 1:
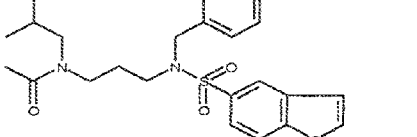
Figure 1:
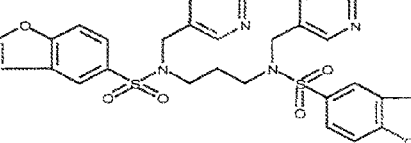
Figure 1:
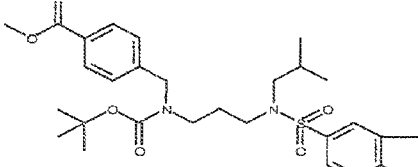
Figure 1:
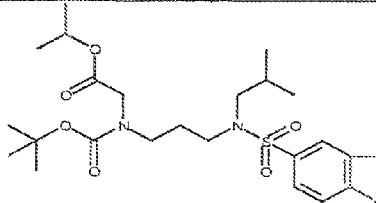
Figure 1:
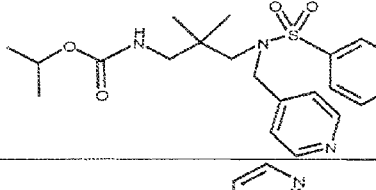
Figure 1:
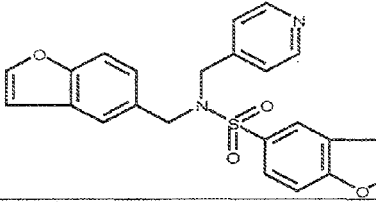
Figure 1:
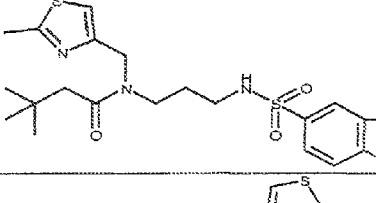
Figure 1:
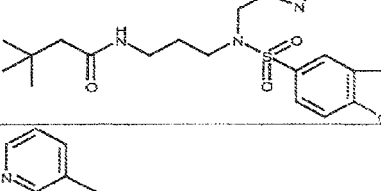
Figure 1:
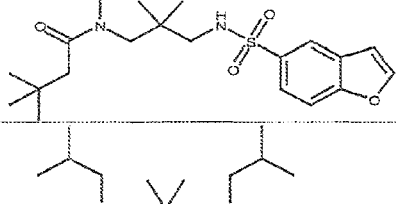
Figure 1:
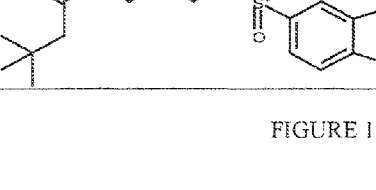
Figure 1:
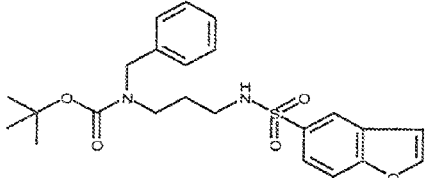
Figure 1:
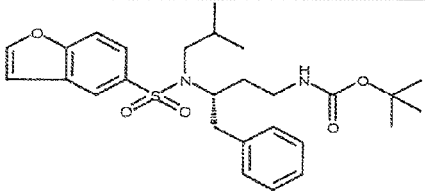
Figure 1:
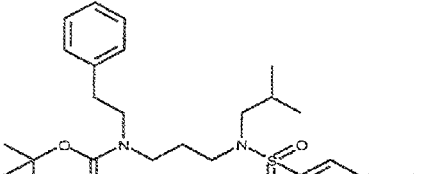
Figure 1:
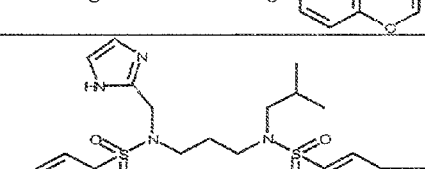
Figure 1:
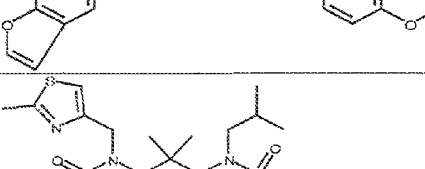
Figure 1:
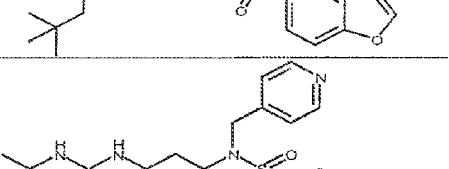
Figure 1:
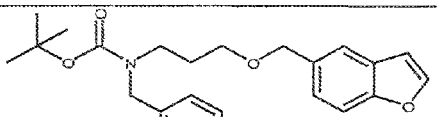
Figure 1:
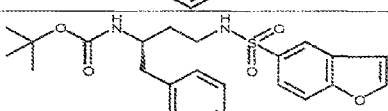
Figure 1:
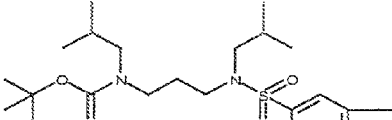
Figure 1:
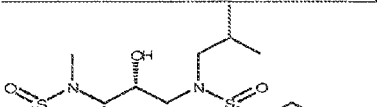
Figure 1:
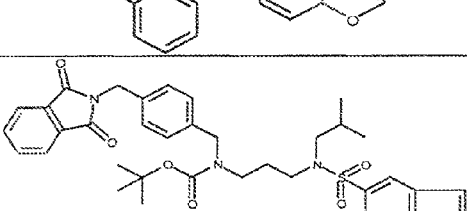
Figure 1:
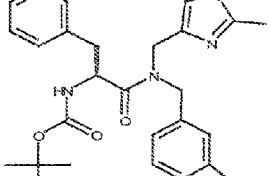
Figure 1:
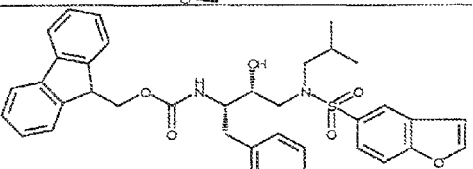
Figure 1:
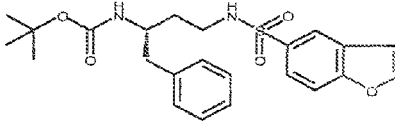
Figure 1:
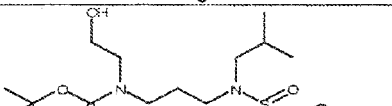
Figure 1:
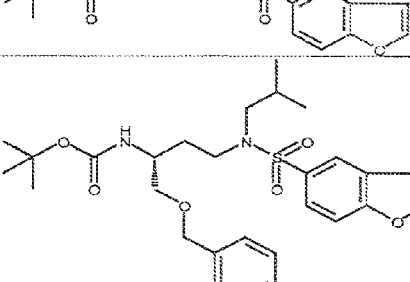
Figure 1:
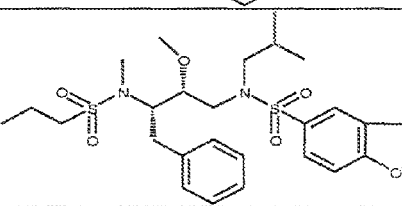
Figure 1:
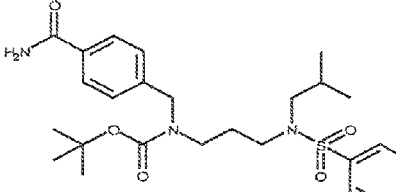
Figure 1:
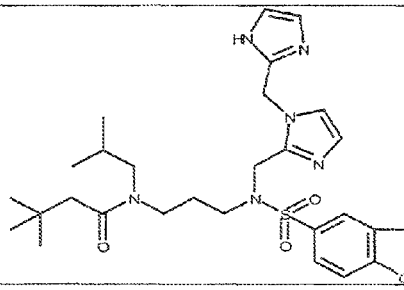
Figure 1:
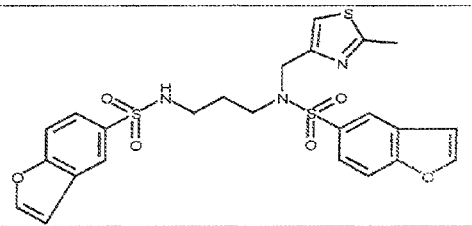
Figure 1:
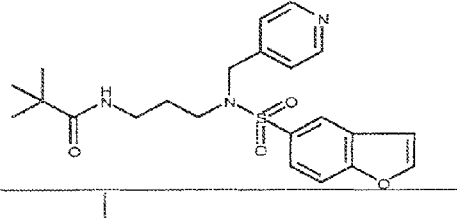
Figure 1:
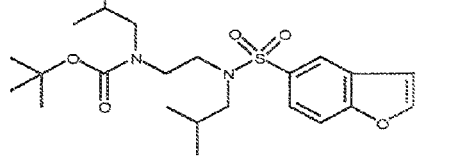
Figure 1:
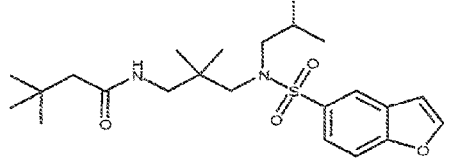
Figure 1:
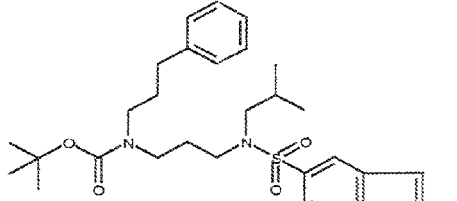
Figure 1:
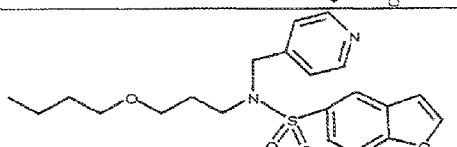
Figure 1:
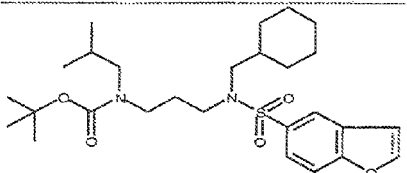
Figure 1:
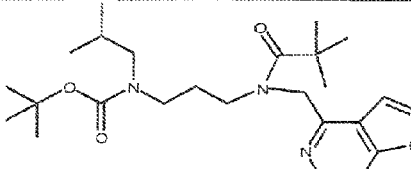
Figure 1:
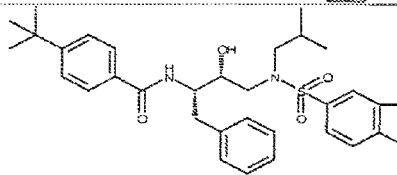
Figure 1:
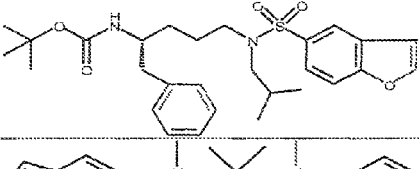
Figure 1:
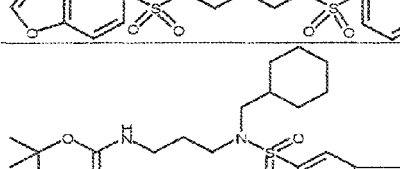
Figure 1:
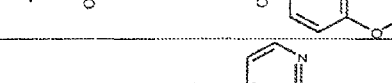
Figure 1:
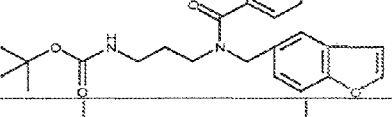
Figure 1:
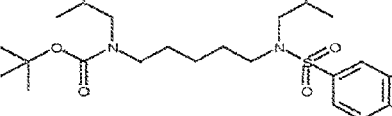
Figure 1:
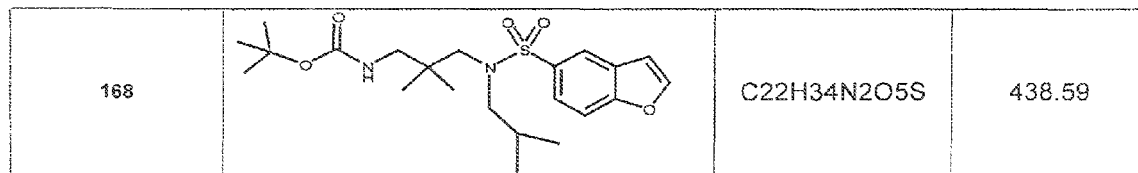

The technology provides methods of inhibiting cytochrome P450 (CYP) enzymes. More particularly, the technology provides methods for enhancing the therapeutic effect of drugs in which the efficacy is compromised due to degradation mediated by cytochrome P450. The methods include administering compounds or pharmaceutical compositions containing the compounds in any therapeutic regimen where one or more primary drugs is metabolized by a CYP. The compounds or pharmaceutical compositions can be administered when the primary drug either becomes inactive or is converted to a toxic metabolite due to metabolism by a CYP.

The compounds or compositions can inhibit or reduce the rate of degradation of drugs that are effective against a variety of diseases and that are degraded by one or more cytochrome P450 enzymes. Upon co-administration, the compounds and compositions can, for example, maintain intracellular concentrations of the drugs at a therapeutic level for a sustained period of time. The methods are useful, for example, in treating a variety of disorders such as, cardiac arrhythmia, depression, psychosis, chronic pain, and infections such as HIV or HCV. The compounds or compositions can be administered either alone or in combination with drugs such as analgesics, anti-depressants, anti-psychotics, antibiotics, anti-arrythmics, steroids, anesthetics, muscle relaxants, cardiac stimulants, NSAIDs, anti-epileptics, or protease inhibitors, such as HIV or HCV protease inhibitors.

In particular, the technology provides a method of inhibiting cytochrome P450 monooxygenase by administering to a patient, a compound represented by a formula:

X-A-B—X' where:

X is a lipophilic group containing from 1 to 12 carbon atoms optionally containing from 1 to 3 heteroatoms independently selected from the group consisting of O, S, and N, A is selected from the group consisting of a bond, —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, where m is 0-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

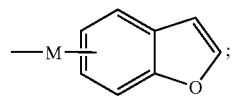

where M is selected from the group consisting of: a bond, OC(R8)$_q$, —CO—, —SO$_n$—, —O—, —O—CO—, —N(D)-SO$_n$—, —N(D)-CO$_n$—, —N(D)-(R8)$_q$-, —SO$_n$—N(D)-(R8)$_q$-, or —CO$_n$—N(D)-(R8)$_q$-, where M can be linked in either orientation with respect to the benzofuran ring, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, where D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, C$_1$-C$_{12}$ alkyl, C$_3$-C$_8$ cycloalkyl, aryl, aralkyl, heteroaryl, heteroaralkyl, and heterocycloalkyl each further optionally substituted with one or more substituents selected from the group consisting of C$_2$-C$_6$ alkenyl, C$_2$-C$_6$ alkynyl, C$_3$-C$_8$ cycloalkyl, C$_5$-C$_8$ cycloalkenyl, heterocyclo; halo, OR, ROH, R-halo, NO$_2$, CN, CO$_n$R, CON(R)$_2$, C(S)R, C(S)

N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

or each R2 is independently selected from the group consisting of C$_1$-C$_6$ alkyl; substituted by aryl or heteroaryl; which groups optionally are substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

R3 is C$_2$-C$_6$ alkenyl, C$_2$-C$_6$ alkynyl, C$_3$-C$_8$ cycloalkyl, C$_5$-C$_8$ cycloalkenyl, or heterocyclo; which groups optionally are substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, oxo, =N—OR2, =N—N(R2)$_2$, =NR2, =NNRC(O)N(R2)$_2$, =NNR2C(O)$_n$R2, =NNR2S(O)$_n$N(R2)$_2$, and =NNR2S(O)$_n$(R2);

R6 is aryl or heteroaryl, where the aryl or heteroaryl optionally are substituted with one or more groups selected from the group consisting of aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, OC(O)R2, OC(S)R2, OC(O)N(R2)$_2$, and OC(S)N(R2)$_2$;

R7 is H, oxo, C$_1$-C$_{12}$ alkyl; C$_3$-C$_8$ cycloalkyl, aryl, aralkyl, heteroaryl, heteroaralkyl, or heterocycloalkyl, each further optionally substituted with one or more substituents selected from the group consisting of C$_2$-C$_6$ alkenyl, C$_2$-C$_6$ alkynyl, C$_3$-C$_8$ cycloalkyl, C$_5$-C$_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and q=0-1, where the benzene ring of the benzofuran moiety may optionally by substituted by up to three substituents independently selected from the group consisting of R2, halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, and NRPO$_n$OR, where the up to three substituents do not form a ring between any adjacent carbon atoms of the benzene ring, and with the proviso that the compound does not contain a basic aliphatic amine function and does not contain a carboxylic acid group.

In a specific embodiment, the invention provides methods of inhibiting cytochrome P450 monooxygenase in a patient by administering to the patient a compound represented by the formula:

X-A-B—X' where:

X is a lipophilic group containing from 1 to 12 carbon atoms optionally containing from 1 to 3 heteroatoms independently selected from the group consisting of O, S, and N, A is —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, where m is 2-6 and where each G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

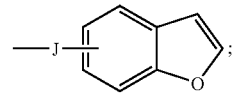

where J is selected from:
—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, wherein D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, C$_1$-C$_{12}$ alkyl, C$_3$-C$_8$ cycloalkyl, aryl, aralkyl, heteroaryl, heteroaralkyl, and heterocycloalkyl each further optionally substituted with one or more substituents selected from the group consisting of C$_2$-C$_6$ alkenyl, C$_2$-C$_6$ alkynyl, C$_3$-C$_8$ cycloalkyl, C$_5$-C$_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

or each R2 is independently selected from the group consisting of C$_1$-C$_6$ alkyl; substituted by aryl or heteroaryl; which groups optionally are substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2—OH, R2-halo, $NO_2$, CN, $CO_n$R2, C(O)N(R2)$_2$, C(O)N(R2)N(R2)$_2$, C(S)R2, C(S)N(R2)$_2$, S(O)$_n$N(R2)$_2$, SR2, $SO_n$R2, N(R)$_2$, N(R2)$CO_n$R2, NR2S(O)$_n$R2, NR2C[=N(R2)]N(R2)$_2$, N(R2)N(R2)$CO_n$R2, oxo, =N—OR2, =N—N(R2)$_2$, =NR2, =NNRC(O)N(R2)$_2$, =NNR2C(O)$_n$R2, =NNR2S(O)$_n$N(R2)$_2$, and =NNR2S(O)$_n$(R2);

R6 is aryl or heteroaryl, where the aryl or heteroaryl optionally are substituted with one or more groups selected from the group consisting of aryl, heteroaryl, R2, R3, halo, OR2, R2OH, R2-halo, $NO_2$, CN, $CO_n$R2, C(O)N(R2)$_2$, C(O)N(R2)N(R2)$_2$, C(S)R2, C(S)N(R2)$_2$, S(O)$_n$N(R2)$_2$, SR2, $SO_n$R2, N(R)$_2$, N(R2)$CO_n$R2, NR2S(O)$_n$R2, NR2C[=N(R2)]N(R2)$_2$, N(R2)N(R2)$CO_n$R2, OC(O)R2, OC(S)R2, OC(O)N(R2)$_2$, and OC(S)N(R2)$_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_n$R, CON(R)$_2$, C(S)R, C(S)N(R)$_2$, $SO_n$N(R)$_2$, SR, $SO_n$R, N(R)$_2$, N(R)$CO_n$R, NRS(O)$_n$R, NRC[=N(R)]N(R)$_2$, N(R)N(R)$CO_n$R, $NRPO_n$N(R)$_2$, $NRPO_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and
where q=0-1.

In another aspect, X may be alkyl, alkenyl, alkynyl, alkoxyalkyl, cycloalkyl, cycloalkylalkyl, heterocycloalkyl, heteroaryl, heterocycloalkylalkyl, aryl, aralkyl, or heteroaralkyl; where X optionally is substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_n$R, CON(R)$_2$, C(S)R, C(S)N(R)$_2$, $SO_n$N(R)$_2$, SR, $SO_n$R, N(R)$_2$, N(R)$CO_n$R, NRS(O)$_n$R, NRC[=N(R)]N(R)$_2$, N(R)N(R)$CO_n$R, $NRPO_n$N(R)$_2$, $NRPO_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R). In one embodiment, X may be selected from the group consisting of alkyl, cycloalkyl, aryl, aralkyl, heteroaryl, and heteroaralkyl. X optionally is substituted with one or more substituents selected from the group consisting of halo, OR, ROH, R-halo, CN, $CO_n$R, CON(R)$_2$, $SO_n$N(R)$_2$, SR, $SO_n$R, N(R)$_2$, N(R)$CO_n$R, NRS(O)$_n$R, oxo, and =N—OR.

In other aspects, $G_1$ and $G_2$ may be the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl. In specific embodiments, $G_1$ and $G_2$ do not form a ring, or at least one $G_1$ and at least one $G_2$ form a ring. $G_1$ and $G_2$ may be different and, in certain embodiments, neither $G_1$ nor $G_2$ is OH.

In other aspects G1 and G2 are selected from the group consisting of H, O-alkyl, alkyl, optionally substituted aryl and optionally substituted aralkyl.

In the embodiments above, J may be —N(D)-$SO_n$—, —N(D)-$CO_n$—, —N(D)-(R8)$_q$-, —N(CO-D)-(R8)$_q$-, —N($SO_n$-D)-(R8)$_q$-, —$SO_n$—N(D)-(R8)$_q$-, or —$CO_n$—N(D)-(R8)$_q$-.

In the embodiments above, D may be hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, or N(R2)-heteroaralkyl, N(R2)-aralkyl, where D optionally is substituted by alkyl, halo, nitro, cyano, O-alkyl, or S-alkyl.

In the compounds, when X is a 5-7 membered non-aromatic monocyclic heterocycle, optionally fused or bridged with one or more 3-7 membered non-aromatic monocyclic heterocycle to form a polycyclic system, where any of the heterocyclic ring systems contains one or more heteroatoms selected from O, N, S, and P, and when B is

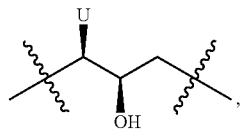

where U is selected from optionally substituted alkyl, optionally substituted alkenyl, optionally substituted alkynyl, optionally substituted aryl, optionally substituted cycloalkyl, or optionally substituted aralkyl, then J cannot be —N(D)-$SO_n$— or —N(D)-$CO_n$.

In the methods described above, the cytochrome P450 monoxygenase may be CYP3A4 or CYP3A5.

In other embodiments, the compound used in the methods described above does not inhibit HIV protease. In the context of the present invention, a compound is said to not inhibit HIV protease when the Ki of the compound is greater than about 1 μM. Such a Ki means that the compound is not clinically useful for inhibiting HIV protease in a patient infected with HIV.

In specific embodiments, the patient may be suffering from chronic pain, depression, epilepsy, psychosis, inflammation, cancer, cardiovascular disease, diabetes, and/or infection, for example, infection with a hepatitis-causing virus or HIV.

In other embodiments, the compound is administered substantially contemporaneously with a drug where efficacy of the drug is compromised due to degradation by cytochrome P450 monooxygenase.

This technology also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products can be obtained by such quaternization.

By way of illustration, but not of limitation, an exemplary CYP inhibitor according to the technology has the structure:

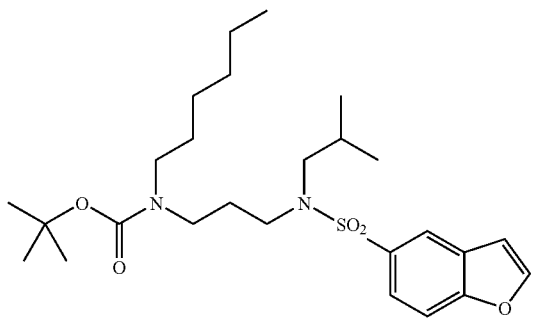

In this molecule, D is isobutyl, B is —(CH$_2$)$_3$, A is —OCON(n-hexyl)-, and X is t-butyl. Certain CYP inhibitors that contain a hydroxyethylene moiety are simultaneously HIV protease inhibitors. These compounds also can be represented by the formula X-A-B—X' with the requirement that B must contain a hydroxyethylene group, i.e. one G group must be a hydroxyl and an adjacent G group must be H. Typically, a CYP inhibitor is found to exhibit HIV protease inhibitor activity when B has the structure: —CH(G)CH(OH)CH$_2$— where G in this instance is not OH, and typically, though not necessarily, is aralkyl. Advantageously X is a bis-etrahydrofuranyl moiety and A is a urethane linker.

The table below shows examples of various X, A, B and J moieties, although it will be recognized that these examples are merely illustrative and not limiting of the present invention.

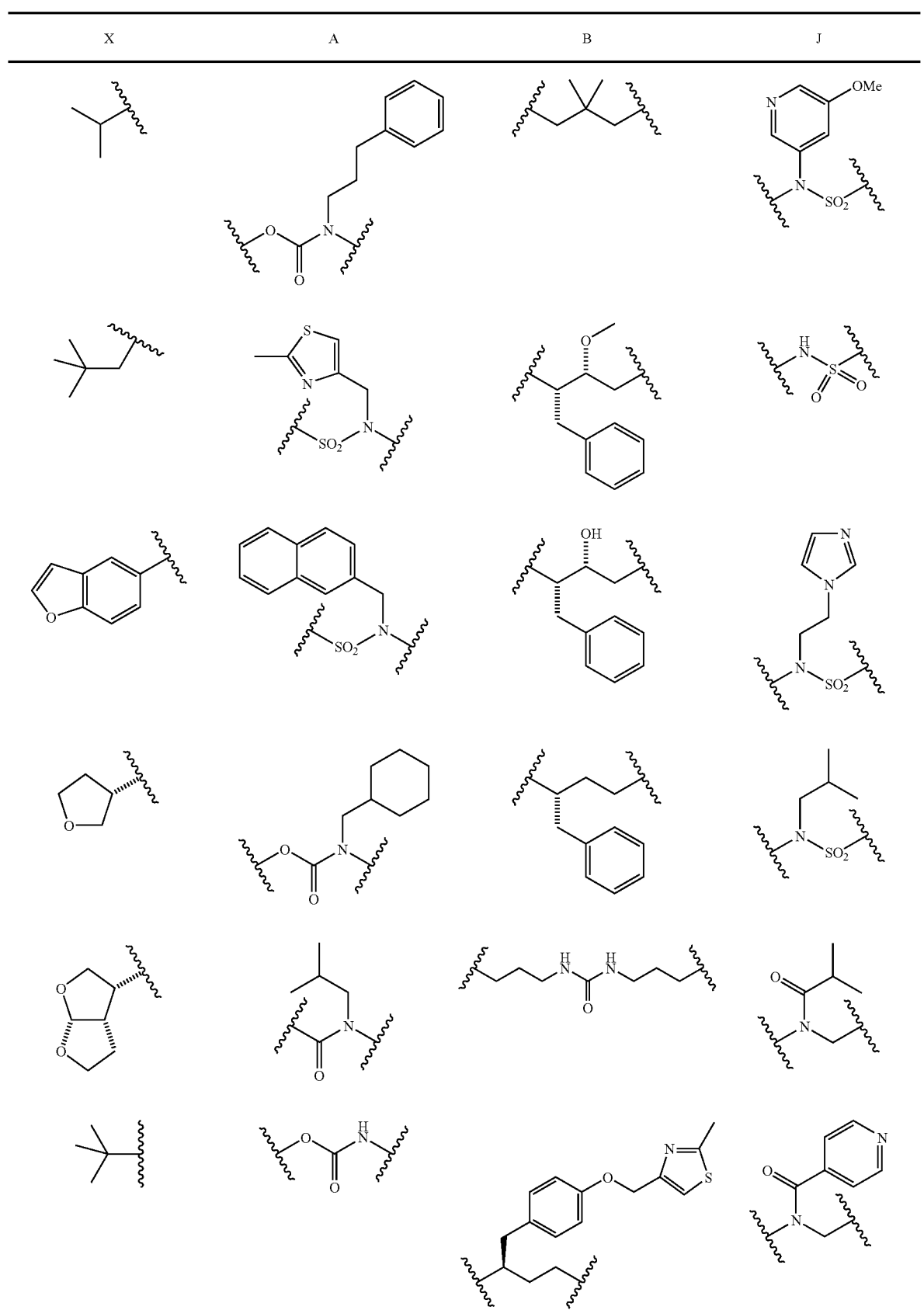

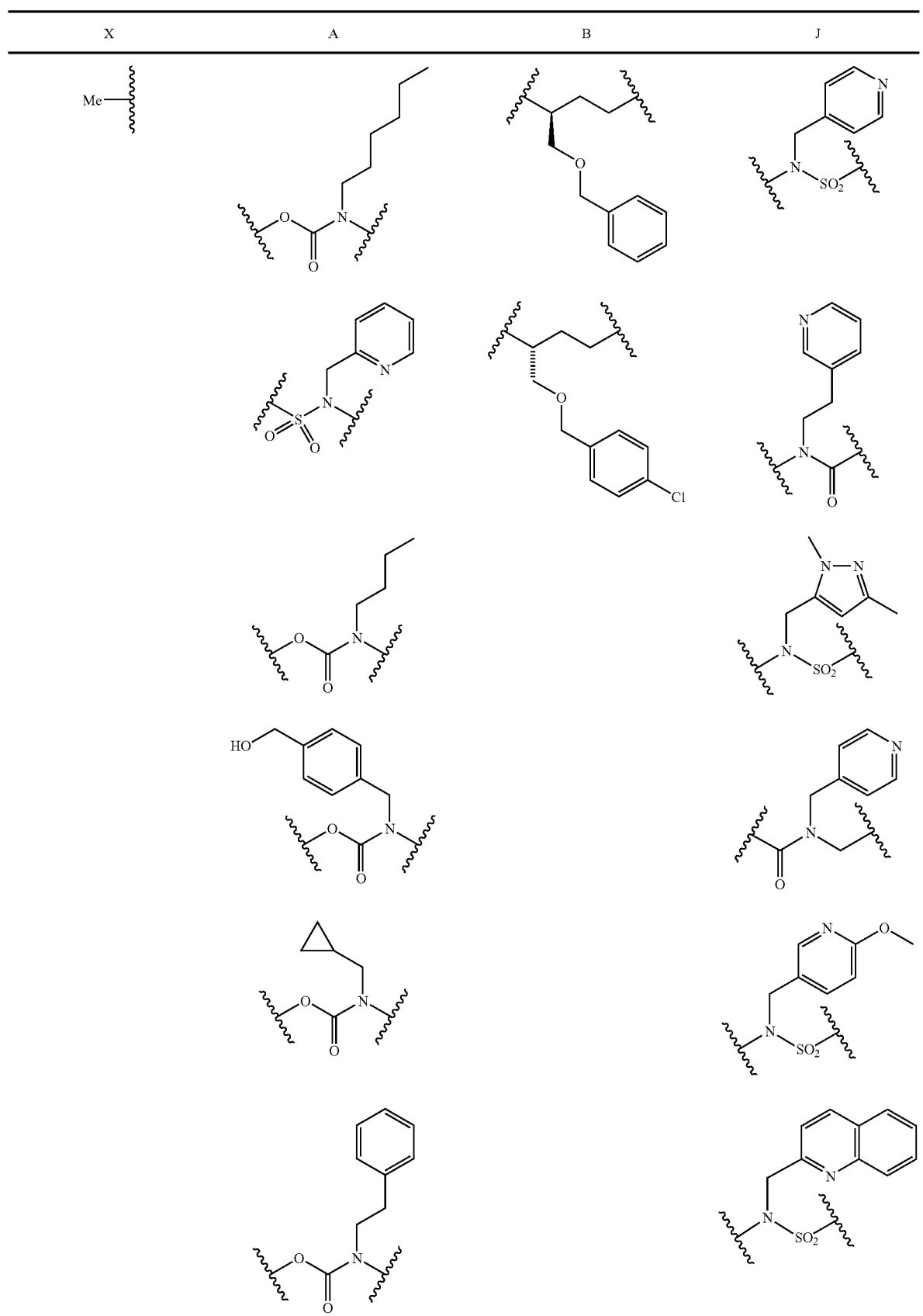

-continued
| X | A | B | J |
|---|---|---|---|
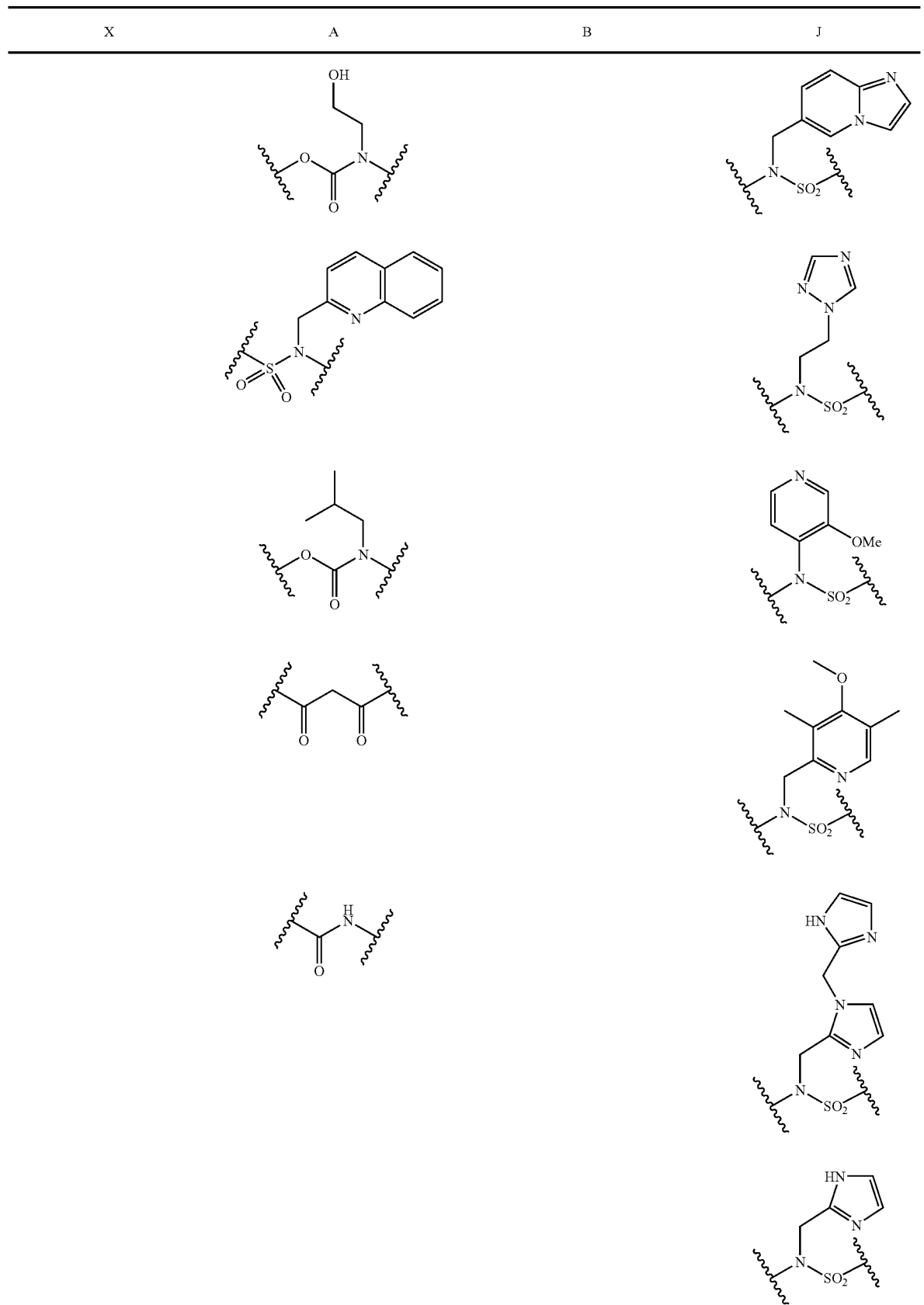

| X | A | B | J |
|---|---|---|---|
|   |   |   | 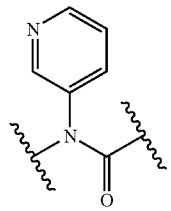 |

The term "pharmaceutically effective amount" or "therapeutically effective amount" or "therapeutic dose" or "efficacious dose" refers to an amount that when administered to a subject is effective in inhibiting cytochrome P450 enough to reduce or prevent the in vivo degradation of a co-administered drug and thereby improve the pharmacokinetics of the drug and/or boost its efficacy. The term "treating" as used herein refers to the alleviation of symptoms of a particular disorder in a subject, such as a human patient, or the improvement of an ascertainable measurement associated with a particular disorder. The term "prophylactically effective amount" refers to an amount effective in preventing an infection, for example an HIV infection, in a subject, such as a human patient. As used herein, a "subject" refers to a mammal, including a human.

The term "lipophilic group" as used herein refers to a group that, when a part of a compound, increases the affinity or propensity of the compound to bind, attach or dissolve in fat, lipid or oil rather than water. A measure of the lipophilicity or hydrophobicity of compounds of the technology can be calculated using the Hansch equation:

$$\text{Log } 1/C = kP$$

where C is the concentration of a compound in a given solvent and P is the hydrophobicity. Details of this method can be obtained from *J. Amer. Chem. Soc*, 86:5175 (1964) and DRUG DESIGN I, edited by E. J. Ariens, Academic Press (1971), both of which are hereby incorporated by reference in their entireties.

Examples of a typical lipophilic group include, but are not limited to, alkyl groups such as methyl, ethyl, n-propyl, isopropyl, n-butyl, isobutyl, t-butyl, n-pentyl, isopentyl, neopentyl, amyl, n-hexyl, n-heptyl, cyclohexyl, cycloheptyl, octyl, nonyl, decyl, undecyl, and dodecyl, alkenes such as ethylene, propylene, butene, pentene, hexene, cyclohexene, heptene, cycloheptene, octene, cyclooctene, nonene, decene, undecene, dodecene, 1,3-butadiene, alkynes such as propyne and butyne, aryls such as phenyl, naphthyl, anthracenyl, phenanthrenyl, fluorenyl, aralkyls such as benzyl, heterocyclyls such as tetrahydrothiophene, dihydrobenzofuran, heteroaryls such as pyrrole, furan, thiophene, pyrazole, thiazole, indole, carbazole, benzofuran, benzothiophene, indazole, benzothiazole, purine, pyridine, pyridazine, pyrazine, triazine, quinoline, acridine, isoquinoline, and phenanthroline.

For small groups containing heteroatom substituents, such as small heterocycles with a high ratio of heteroatoms to carbon atoms, the introduction of substituents that reduce the heteroatom to carbon atom ratio renders the group lipophilic. For example, a triazole ring can be rendered more lipophilic by the introduction of alkyl substituents. Similarly, non-lipophilic substituents such as hydroxy or amido can be rendered lipophilic by introducing additional carbon atoms, for example by exchanging a hydroxymethyl group to a hydroxybenzyl group, or by exchanging a carboxamido group to a dialkyl carboxamido group.

The term "substituted", whether preceded by the term "optionally" or not, and substitutions contained in formulas of this technology, include the replacement of one or more hydrogen radicals in a given structure with the radical of a specified substituent. When more than one position in a given structure can be substituted with more than one substituent selected from a specified group, the substituents can be either the same or different at every position (for example, in the moiety —N(R2)(R2), the two R2 substituents can be the same or different). Typically, when a structure can be optionally substituted, 0-3 substitutions are preferred, and 0-1 substitution is more preferred. Advantageously, each substituent enhances cytochrome P450 inhibitory activity in permissive mammalian cells, or enhances deliverability by improving solubility characteristics or pharmacokinetic or pharmacodynamic profiles as compared to the unsubstituted compound. Combinations of substituents and variables envisioned by this technology are limited to those that result in the formation of stable compounds.

The term "stable", as used herein, refers to compounds which possess stability sufficient to allow manufacture, formulation, and administration to a mammal by methods known in the art. Typically, such compounds are stable at a temperature of 40° C. or less, in the absence of moisture or other chemically reactive conditions, for at least a week.

The term "alkyl", alone or in combination with any other term, refers to a straight-chain or branched-chain saturated aliphatic hydrocarbon radical containing the specified number of carbon atoms, or where no number is specified, advantageously from 1 to about 12 or 1 to 15 carbon atoms. Examples of alkyl radicals include, but are not limited to: methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, advantageously from 2-6 or 2-10 carbon atoms. Alkenyl groups include all possible E and Z isomers unless specifically stated otherwise. Examples of alkenyl radicals include, but are not limited to, ethenyl, propenyl, isopropenyl, butenyl, isobutenyl, pentenyl, hexenyl, hexadienyl and the like.

The term "alkynyl," alone or in combination with any other term, refers to a straight-chain or branched-chain hydrocarbon radical having one or more triple bonds containing the specified number of carbon atoms, or where no number is specified, advantageously from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, where the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The terms "alkylamino" or "dialkylamino" include amino radicals substituted by one or two alkyl groups, where the term "alkyl" is defined above, and the alkyl group can be the same or different. Examples of suitable alkylamino and dialkylamino radicals include, but are not limited to, methylamino, ethylamino, isoproylamino, dimethylamino, methylethylamino, ethylbutylamino and the like.

The term "hydroxyalkyl" refers to an alkyl radical as defined above in which one of the hydrogen atoms is replaced by hydroxy group. Examples of suitable hydroxyalkyl radicals include, but are not limited to, hydroxymethyl, 2-hydroxypropyl and the like.

The term "alkoxyalkyl" refers to an alkyl radical as defined above in which one of the hydrogen atoms is replaced by an alkoxy radical as defined above.

The terms "aminoalkyl", "alkylaminoalkyl" or "dialkylaminoalkyl" refers to an alkyl radical as defined above in which one of the hydrogen atoms is replaced by an amino or "alkylamino" or "dialkylamino" radical as defined above.

The term "halo" or "halogen" includes fluorine, chlorine, bromine or iodine.

The term "haloalkyl" includes alkyl groups with one or more of its hydrogens replaced by halogens.

The term "thioalkyl" includes alkyl radicals having at least one sulfur atom, where alkyl has the significance given above. An example of a thioalkyl is $CH_3SCH_2$. The definition also encompasses the corresponding sulfoxide and sulfone of this thioalkyl $CH_3S(O)CH_2$ and $CH_3S(O)_2CH_2$ respectively. Unless expressly stated to the contrary, the terms "—$SO_2$—" and "—$S(O)_2$—" as used herein include sulfone or sulfone derivative (i.e., both appended groups linked to the S), and not a sulfinate ester.

The terms "carboalkoxy" or "alkoxycarbonyl" include alkyl esters of a carboxylic acid. Examples of "carboalkoxy" or "alkoxycarbonyl" radicals include, but are not limited to ethoxycarbonyl (or carboethoxy), Boc (or t-butoxycarbonyl), Cbz (or benzyloxycarbonyl) and the like.

The term "alkanoyl" includes acyl radicals derived from an alkanecarboxylic acid. Examples of alkanoyl radicals include, but are not limited to, acetyl, propionyl, isobutyryl and the like.

The term "aryl," alone or in combination with any other term, refers to a carbocyclic aromatic radical (such as phenyl or naphthyl) containing the specified number of carbon atoms, preferably from 6-15 carbon atoms, and more preferably from 6-10 carbon atoms, optionally substituted with one or more substituents selected from alkyl, alkoxy, (for example methoxy), nitro, halo, amino, mono or dialkylamino, carboalkoxy, cyano, thioalkyl, alkanoyl, carboxylate, and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, includes alkyl radicals as defined above in which one or more hydrogen atoms is replaced by an aryl radical as defined above. Examples of aralkyl radicals include, but are not limited to benzyl, 2-phenylethyl and the like.

The term "aralkanoyl" includes acyl radicals derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, (1-naphthyl)acetyl, 4-methoxyhydrocinnamoyl, and the like.

The term "aroyl" includes acyl radicals derived from an aromatic carboxylic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "arylsulfonyl" includes sulfonyl radicals derived from an aromatic sulfonic acid such as benzenesulfonyl, 4-chlorobenzenesulfonyl, 1-naphthalenesulfonyl, 2-naphthalenesulfonyl, and the like.

The term "carbocycle" refers to a non-aromatic stable 3- to 8-membered carbon ring which can be saturated, mono-unsaturated or poly-unsaturated. The carbocycle can be attached at any endocyclic carbon atom which results in a stable structure. Preferred carbocycles have 5-7 carbons.

The term "cycloalkyl", alone or in combination, includes alkyl radicals which contain from about 3 to about 8 carbon atoms and are cyclic. Examples of such cycloalkyl radicals include cyclopropyl, cyclobutyl, cyclopentyl, cyclohexyl and the like.

The term "cycloalkenyl" alone or in combination includes alkenyl radicals as defined above which contain about 3-8 carbon atoms and are cyclic.

The term "cycloalkylalkyl" includes alkyl radicals as defined above which are substituted by a cycloalkyl radical containing from about 3 to about 8, preferably from about 3 to about 6, carbon atoms.

The term "heterocyclyl" or "heterocyclo" or "heterocycloalkyl" refers to a stable 3-7 membered monocyclic heterocycle or 8-11 membered bicyclic heterocycle which is either saturated or partially unsaturated, and which can be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include oxidized forms of nitrogen and sulfur, and the quaternized form of any basic nitrogen. A heterocyclyl radical can be attached at any endocyclic carbon or heteroatom which results in the creation of a stable structure. Preferred heterocycles include 5-7 membered monocyclic heterocycles, and 8-10 membered bicyclic heterocycles. Examples of such groups imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroaryl" refers to stable 5-6 membered monocyclic or 8-11 membered bicyclic or 13-16 membered tricyclic aromatic heterocycles where heterocycles is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiazolyl, thiadiazyl, oxathiolyl, acridinyl, phenanthridinyl, and benzocinnolinyl.

The term "heterocycloalkylalkyl" refers to an alkyl radical as defined above which is substituted by a heterocycloalkyl radical as defined above.

The term "heteroaralkyl" alone or in combination, includes alkyl radicals as defined above in which one or more hydrogen atom is replaced by a hetoaryl group as defined above.

As used herein, the compounds of this technology are defined to include pharmaceutically acceptable derivatives or prodrugs thereof. A "pharmaceutically acceptable derivative or prodrug" includes a pharmaceutically acceptable salt, ester, salt of an ester, or other derivative of a compound of this technology which, upon administration to a recipient, is capable of providing (directly or indirectly) a compound of this technology. Particularly favored derivatives and prodrugs are those that increase the bioavailability of the compounds of this technology when such compounds are administered to a mammal (e.g., by allowing an orally administered compound to be more readily absorbed into the blood) or which enhance delivery of the parent compound to a biological compartment (e.g., the brain or lymphatic system) relative to the parent species. Examples of prodrugs of hydroxy containing compounds are amino acid esters or phosphonate or phosphate esters that can be cleaved in vivo hydrolytically or enzymatically to provide the parent compound. These have the advantage of providing potentially improved solubility.

The compounds of this technology can contain one or more asymmetric carbon atoms and thus occur as racemates and racemic mixtures, single enantiomers, diastereomeric mixtures and individual diastereomers. All such isomeric forms of these compounds are expressly included in the technology. Each stereogenic carbon can be of the R or S configuration. Although the specific compounds exemplified in this application can be depicted in a particular stereochemical configuration, compounds having either the opposite stereochemistry at any given chiral center or mixtures thereof are also envisioned.

Preparation of the Compounds

The compounds can be prepared according to synthetic methods set forth, for example, in U.S. Pat. No. 6,319,946 to Hale et al., and in *J. Med. Chem.* 36, 288-291 (93), the disclosures of which are incorporated herein by reference in their entireties, together with procedures of the type described below.

Condensation of hydroxyethylamine A with benzofuran-5-sulfonyl chloride provided compound 36. This material can be selectively O-alkylated in the presence of base and an alkylating agent such as iodomethane to provide compound 5. See Barrish, et al. *J. Med. Chem.* 1758-1768 (1994). Further alkylation on the urethane nitrogen can be accomplished using excess base and alkylating agent. Removal of the Boc group under acidic conditions such as trifluoroacetic acid provides the amine which is subject to condensation with acid chlorides, anhydrides, sulfonyl chlorides, chloroformates, carbamoyl chloride, isocyanates and the like to provide the corresponding amide, sulfonamide, urethane, or urea. Alternatively, reductive amination of the amine with an aldehyde under acidic conditions can provide the secondary amine which can be subjected to similar condensation reactions to give the N-alkyl products (e.g. N-alkyl amide).

Other amines besides isobutylamine can be used to ring open the epoxide leading to different N-substituted sulfonamides as the products.

Homologation of Boc-phenylalaminol using a mesylation, cyanide, reduction, reductive alkylation protocol provided Boc-diamine 224, which was treated with benzofaran-5-sulfonyl chloride as above. See Lim et al., Bioorg. Med. Chem. Lett., 1913-1916 (2004), Dallaire et al. Tetrahedron Lett 5129-5132 (1998), Mecozzi et al., J. Org. Chem. 8264-8267 (2001). Alternatively the amine from the reduction can first be sulfonylated, followed by N-alkylation on the sulfonamide nitrogen in the presence of a strong base. Additional base and alkylating agent can provide alkylation of the urethane nitrogen. The Boc group can be removed under acidic conditions either on either the NH or N-alkyl intermediate and the products further elaborated as above by condensation with acid chlorides, anhydrides, sulfonyl chlorides, chloroformates, carbamoyl chloride, or isocyanates. Alternatively the ethylene diamine analogs of these compounds can be prepared by reacting the activated phenylalaminol with azide instead of cyanide followed by reduction as in Rosenberg, et al., J. Med. Chem. 1582-1590 (1990). Elaboration of this core is as above.

The benzyl group in the core can be replaced by a benzyloxymethyl group by reducing the commercially available doubly protected Boc-Cbz-diaminobutyric acid analog to give the alcohol, removing the Cbz protecting group and sulfonylating the resulting amine as above. See Webber et al., J. Med. Chem. 2786-2805 (1998), Catalano, et al., Bioorg. Med. Chem. Lett., 275-278 (2004). Alkylating the hydroxy group using a strong base such as sodium hydride and an alkylating agent provides ethers such as compound 12. These can be further elaborated as in the examples above.

Alternatively compounds without branching in the diamine core can be prepared by taking the well known Boc-diamines, and condensing with benzofuransulfonyl chloride. See Fiedler, et al.; Helv. Chim. Acta 1511-1519 (1993), Chatterjee, et al., Bioorg. Med. Chem. Lett., (2603-2606) 1999, Saari, et al., J. Med. Chem. 3132-3138 (1991). These products can be N-alkylated on the sulfonamide nitrogen and then optionally on the urethane nitrogen and further elaborated similarly to above. Alternatively the primary amine can be reductively aminated using an aldehyde under reducing conditions and then condensed with benzofuransulfonyl chloride to provide similar products.

The potency of the compounds can be measured using assays, for example, an in vitro fluorometric assay. Typically, the ability of a test compound to inhibit P450 is assayed by determining the concentration of the test compound required to decrease the maximal rate of metabolism of a CYP substrate (also referred to herein as reference compound) by half. The CYP substrate can be, for example, dibenzylfluorescein. The ability of a test compound to inhibit the maximal rate of metabolism of a reference compound by half is known as the $IC_{50}$ value. Human liver microsomes can be used for this purpose. Test compounds can be diluted with a suitable solvent, such as acetonitrile, in wells of a micro-titer plate. Known Cytochrome P450 inhibitors such as Ritonavir and ketoconazole can be used as references. A suitable buffer solution and a NADPH generating system such as, for example, G6P dehydrogenase can be used. After mixing the inhibitors with the buffer and NADPH system, the plates can be incubated for a suitable time at a suitable temperature. A solution containing human liver microsomes can be added. A buffer containing a fluorogenic substrate, such as dibenzylfluorescein, can be added and the plates allowed to incubate for a suitable time at a suitable temperature. The $IC_{50}$ values for the test compounds can be measured by determining the amount of fluorescence in each well and analyzing the values using commercially available software programs such as, for example, Grafit® (Erithacus Software Ltd., Surrey, U.K.).

Use of Compounds of the Technology for "Boosting"

Cytochrome P450 enzymes are responsible for the metabolic degradation of a variety of drug molecules, thus disturbing their pharmacokinetics and reducing their bioavailbilty. Compositions that can inhibit cytochrome P450 can therefore improve the pharmacokinetics and bioavailability of such drugs.

In certain embodiments, the technology provides methods for inhibiting cytochrome P450 monooxygenase by administering to a patient one or more compounds described herein.

The compound can function as a potent cytochrome P450 inhibitor and can improve the pharmacokinetics of a drug (or a pharmaceutically acceptable salt thereof) which is metabolized by cytochrome P450 monooxygenase. The compound or its pharmaceutically acceptable salt can be administered by itself or in combination with the other drug. When administered in combination, the two therapeutic agents can be formulated as separate compositions which are administered at the same time or different times, or the two therapeutic agents can be administered as a single composition.

The compounds of the technology are effective for inhibiting a variety of CYP enzymes. In particular, many of the compounds are highly potent inhibitors of CYP3A4, which is responsible for degrading many pharmaceutically important drugs. Use of the compounds of the technology therefore permits reduced rates of drug degradation and consequently extended durations of action in vivo. Consequently, these compounds are useful for "boosting" the activities of a variety of drugs, including, but not limited to, HIV protease inhibitors by inhibiting CYP3A4-mediated degradation of those inhibitors.

Drugs which are metabolized by cytochrome P450 monooxygenase and which benefit from coadministration with a compound of the technology include, but are not limited to, the immunosuppressants cyclosporine, FK-506 and rapamycin, the chemotherapeutic agents taxol and taxotere, the antibiotic clarithromycin and the HIV protease inhibitors A-77003, A-80987, indinavir, saquinavir, amprenavir, nelfinavir, fosamprenavir, lopinavir, atazanavir, darunavir, tipranavir, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), and KNI-272.

In certain embodiments, there is disclosed a method for improving the pharmacokinetics of an HIV protease inhibitor (or a pharmaceutically acceptable salt thereof) which is metabolized by cytochrome P450 monooxygenase comprising coadministering a compound of the technology or a pharmaceutically acceptable salt thereof. Such a combination of a compound of the technology or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be formulated as separate compositions which are administered at the same time or different times, or the two therapeutic agents can be administered as a single composition.

Methods of Administration of Compounds

The compounds of the technology can be administered in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include salts with an inorganic base, organic base, inorganic acid, organic acid, or basic or acidic amino acid. Inorganic bases which form the pharmaceutically acceptable salts include alkali metals such as sodium or potassium, alkali earth metals such as calcium and magnesium, aluminum, and ammonia. Organic bases which form pharmaceutically acceptable salts include trimethylamine, triethylamine, pyridine, picoline, ethanolamine, diethanolamine, triethanolamine, dicyclohexylamine. Inorganic acids which form the pharmaceutically acceptable salts include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

The technology also contemplates compositions which can be administered orally or non-orally in the form of, for example, granules, powders, tablets, capsules, syrup, suppositories, injections, emulsions, elixirs, suspensions or solutions, by mixing these effective components, individually or simultaneously, with pharmaceutically acceptable carriers, excipients, binders, diluents or the like.

As a solid formulation for oral administration, the composition can be in the form of powders, granules, tablets, pills and capsules. In these cases, the compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

Examples of liquid preparations for oral administration include pharmaceutically acceptable emulsions, syrups, elixirs, suspensions and solutions, which can contain an inactive diluent, for example, water.

As used herein, "non-orally" includes subcutaneous injection, intravenous injection, intramuscular injection, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections can be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The pharmaceutical compositions can be formulated for nasal aerosol or inhalation and can be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

The pharmaceutical composition can be easily formulated for topical administration with a suitable ointment containing one or more of the compounds suspended or dissolved in a carrier, which include mineral oil, liquid petroleum, white petroleum, propylene glycol, polyoxyethylene, polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetaryl alcohol, 2-octyldodecanol, benzyl alcohol and water.

In some embodiments, the pharmaceutical compositions can include α-, β-, or γ-cyclodextrins or their derivatives. In certain embodiments, co-solvents such as alcohols can improve the solubility and/or the stability of the compounds in pharmaceutical compositions. In the preparation of aqueous compositions, addition salts of the compounds can be suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with $C_1$-$C_6$alkyl, such as methyl, ethyl or isopropyl, e.g. randomly methylated β-CD; hydroxy $C_{16}$ alkyl, particularly hydroxy-ethyl, hydroxypropyl or hydroxybutyl; carboxy $C_1$-$C_6$alkyl, particularly carboxymethyl or carboxyethyl; $C_1$-$C_6$alkyl-carbonyl, particularly acetyl; $C_1$-$C_6$ alkyloxycarbonyl$C_1$-$C_6$alkyl or carboxy$C_1$-$C_6$alkyloxy$C_1$-$C_6$alkyl, particularly carboxymethoxypropyl or carboxyethoxypropyl; $C_1$-$C_6$alkylcarbonyloxy$C_1$-$C_6$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxy-propyl-γ-CD and (2-carboxymethoxy)propyl-β-CD, and in particular 2-hydroxypropyl-β-CD (2-HP-β-CD).

The term "mixed ether" denotes cyclodextrin derivatives where at least two cyclodextrin hydroxy groups are etherified with different groups such as, for example, hydroxy-propyl and hydroxyethyl.

The compounds can be formulated in combination with a cyclodextrin or a derivative thereof as described in U.S. Pat. No. 5,707,975. Although the formulations described therein are with antifungal active ingredients, they are equally relevant for formulating compounds of the technology. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations can also be rendered more palatable by adding pharmaceutically acceptable sweeteners and/or flavors.

Other convenient ways to enhance the solubility of the compounds of the technology in pharmaceutical compositions are described in WO 94/05263, WO 98/42318, EP-A-499,299 and WO 97/44014, all incorporated herein by reference.

In some embodiments, the compounds can be formulated in a pharmaceutical composition comprising a therapeutically effective amount of particles consisting of a solid dispersion comprising a compound of formula I, and one or more pharmaceutically acceptable water-soluble polymers.

The term "solid dispersion" defines a system in a solid state comprising at least two components, where one component is dispersed more or less evenly throughout the other component or components. When the dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It can further be convenient to formulate the compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds can also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration can depend on the condition of the subject, co-medication and the like.

Dosages of the compounds are dependent on age, body weight, general health conditions, sex, diet, dose interval, administration routes, excretion rate, combinations of drugs and conditions of the diseases treated, while taking these and other necessary factors into consideration. Generally, dosage levels of between about 10 μg per day to about 5000 mg per day, preferably between about 100 mg per day to about 1000 mg per day of the compound are useful for the inhibition of CYP enzymes. Typically, the pharmaceutical compositions of this technology will be administered from about 1 to about 3 times per day or alternatively, as a continuous infusion. Such administration can be used as a chronic or acute therapy.

The amount of active ingredient that can be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 5% to about 95% active compound (w/w). Preferably, such preparations contain from about 10% to about 80% active compound. The desired unit dose of the composition of this technology is administered once or multiple times daily.

In some embodiments, the technology contemplates compositions and formulations comprising one or more of the compounds in combination with one or more other drugs that can be metabolized or degraded by CYP.

The CYP inhibitors of this technology can be administered to a patient either as a single agent (for use with a separate dose of another drug) or in a combined dosage form with at least one other drug. Additional drugs also can be used to increase the therapeutic effect of these compounds.

The compounds of this technology can be administered to patients being treated with a drug that is metabolized by a CYP enzyme. Such drugs include, but are not limited to, anesthetics such as ropivacaine, enflurane, halothane, isoflurane, methoxyflurane, and sevoflurane; antiarrhythmics such as mexilletine; antidepressants such as amitriptyline, clomipramine, fluvoxamine, bupropion, and imipramine; anti-epileptics such as diazepam, phenyloin, S-mephenyloin, and phenobarbitone; antihistamines such as astemizole, chlorpheniramine, and terfenidine; antipsychotics such as clozapine, olanzapine, and haloperidol; beta blockers such as carvedilol, S-metoprolol, propafenone, and timolol; calcium channel blockers such as amlodipine, diltiazem, felodipine, lercanidipine, nifedipine, nisoldipine, nitrendipine, and verapamil; hypoglycemic agents such as tolbutamide and glipizide; immune modulators such as cyclosporine and tacrolimus; muscle relaxants such as cyclobenzaprine, tizanidine, and carisoprodol; steroids such as estradiol; antimigraine agents such as zolmitriptan; agents used to treat breathing aliments such as zileuton and theophylline; agents used to treat Alzheimer's disease such as tacrine; agents used to treat pain such as naproxen and acetaminophen; agents used to treat amyotrophic lateral sclerosis such as riluzole; anti-nausea agents such as ondansetron; chemotherapeutics such as paclitaxel, ifosfamide, and cyclophosphamide; loop diuretics such as torsemide; antidiabetic agents such as repaglinide; statin, such as cerivastatin; antimalarial agents such as amodiaquine; proton pump inhibitors such as lansoprazole, omeprazole, pantoprazole, and rabeprazole; and sulfonylureas such as glyburide, glibenclamide, glipizide, glimepiride, and tolbutamide. Patients being treated with a protease inhibitor, a viral fusion inhibitor, or an integrase inhibitor can also be treated with the compounds provided herein. The CYP inhibitors provided herein can be co-administered with the other drug(s). The compounds of the technology can also be administered in combination with other cytochrome P450 inhibitors, immunomodulators (e.g., bropirimine, anti-human alpha interferon antibody, IL-2, methionine enkephalin, interferon alpha, HE-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate infections as therapeutically appropriate.

Cyp inhibitors can also be used as standalone therapeutics for Cyp-mediated diseases, or as prophylactic agents for preventing the production of toxic metabolites. For example, an inhibitor of Cyp2A6 or 2A13 can be used to ameliorate the carcinogenic effects of tobacco usage.

Such combination therapy in different formulations can be administered simultaneously, separately or sequentially. The Cyp inhibitors can be administered prior to administration of the other drug to reduce Cyp levels and minimize degradation of the drug. In specific embodiments, the Cyp inhibitor is administered, 30 minutes, 1 hour, four hours, twelve hours or twenty four hours prior to initial administration of the other drug. The Cyp inhibitors tend to have a long half in vivo, presumably as a result of inhibiting their own metabolism. This means that once treatment has begun, the Cyp inhibitor may be administered less frequently than the drug, although the skilled artisan will recognize that different administration regiments may be needed in specific situations. In certain instances, Cyp inhibitors can also induce expression of Cyps and the skilled artisan will appreciate that in such circumstances, administration of the Cyp inhibitor may need to be more frequent. Alternatively, such combinations can be administered as a single formulation, whereby the active ingredients are released from the formulation simultaneously or separately.

The following examples illustrate further the technology but, of course, should not be construed in any way of limiting its scope.

EXAMPLES

Example 1

Assay of $IC_{50}$ for CYP Inhibitors: Determinations using Dibenzylfluorescein Metabolism by Human Liver Microsomes A microtiter plate based, fluorometric assay was used for the determination of the concentration of a test compound that will decrease by half the maximal rate of dibenzylfluorescein, a CYP3A4 substrate, metabolism by human liver microsomes. The assay was run as described by Crespi et al. Anal. Biochem. 248:188-90 (1997).

Test compounds were diluted in acetonitrile in wells of a polypropylene micro-titer plate (Denville Scientific, Inc. Metuchen, N.J.). Three fold serial dilutions of the test article were made from the first well into the next seven wells of a row. Two wells of each row were used for positive controls containing no test compound and two for negatives containing 500 μM Ritonavir in acetonitrile. Test compounds in acetonitrile (0.004 mL) were added to wells of a micro titer plate (Catalog No. 3598, Corning Costar, Cambridge, Mass.) containing a solution (0.096 mL) of 0.2 M KPO4 Buffer (pH 7.4) and a NADPH generating system (2.6 mM NADP, 6.6 mM glucose-6-phosphate, 3.3 mM MgCl2 and 0.8 Units/mL G6P dehydrogenase (BD/Gentest, Woburn, Mass.). The plates were incubated for 10 minutes at 37° C. prior to addition of 0.1 mL of pre-warmed 0.1 mg/mL human liver microsomes (Xeno Tech, LLC, Lenexa, Kans.) in 0.2 M KPO4 Buffer containing 2 μM dibenzylfluorescein (BD/Gentest, Woburn, Mass.). The plates were incubated for 10 minutes at 37° C. and the reaction are stopped by the addition of 0.075 mL of 2N NaOH. Plates were incubated at 37° C. for 1 hours prior to determining the amount of fluorescence in each well with a fluorescent plate reader (Spectra Max Gemini XS, Molecular Devices) at an excitation/emission wavelengths of 485 and 538 nm (25 nm), respectively. Data were exported and analyzed using GraFit® (Erithacus Software Ltd., Surrey, U.K.). The background corrected data is fit to a 2-parameter equation for the determination of the IC50.

Example 2

Synthetic Methods

The following experimental protocols are illustrative of the methods used to synthesize the compounds of the technology. Syntheses of the compounds below are exemplified, although the skilled artisan will recognize that these exemplary methods are of general applicability.

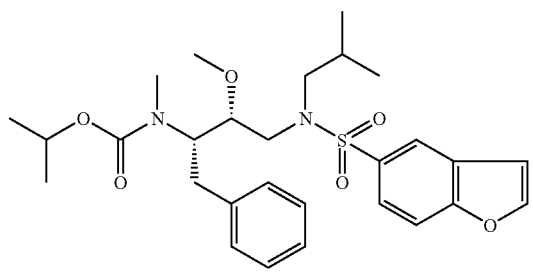

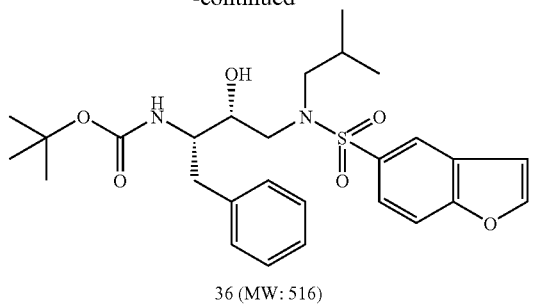

36 (MW: 516)

(1-Benzyl-2-hydroxy-3-isobutylamine-propyl)-carbamic acid tert-butyl ester (SM A, 10.08 g, 30 mmol, 1.0 equiv.) and 1-benzofuran-5-sulfonyl chloride (SM B, 9.74 g, 45 mmol, 1.5 equiv.) were dissolved in dichloromethane (100 mL). To the solution was added triethylamine (8.36 mL, 60 mmol, 2.0 equiv.) at room temperature. The mixture was stirred at the same temperature for 2.5 h, after which time the reaction was quenched through the addition of 0.5 N hydrochloric acid aqueous solution (50 mL). The phases were separated and then the organic layer was sequentially washed with 5% sodium bicarbonate (50 mL) and water (50 mL). The final organic solution was dried over anhydrous sodium sulfate and concentrated in vacuo. The residue was purified by recrystallization from ethyl acetate/hexane (30/90, v/v) to afford a white solid, 13.09 g, m.p. 121.1-122.4° C. The filtrate was concentrated and the residue was purified on silica gel (0-50% ethyl acetate in hexane) to afford 1.13 g additional target compound. Yield 14.22 g (92%). MS 1055 (2MNa)$^+$, 539 (MNa)$^+$, 417 (M-BOC)$^+$ and 575 (AcOM)$^-$. Purity 97% (HPLC).

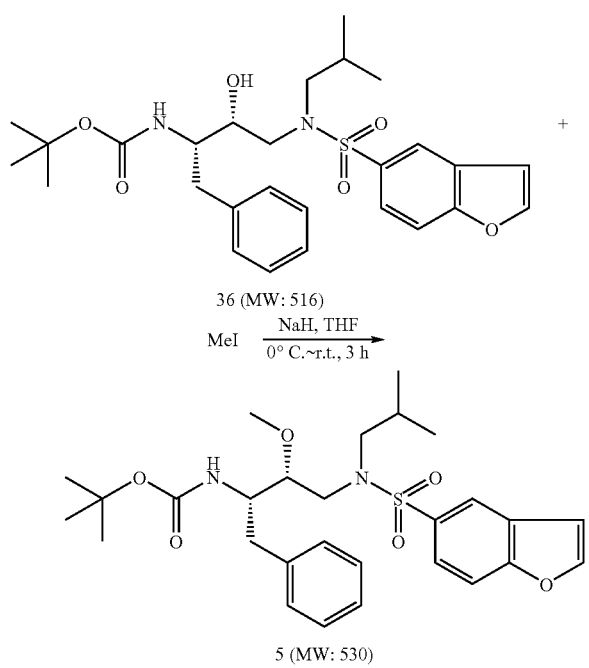

36 (MW: 516)

5 (MW: 530)

A 250 mL three-neck round-bottom flask was equipped with a magnetic stirbar, an argon inlet adapter and an air outlet adapter connected to a bubbler. The flask was charged with compound 36 (12.38 g, 24 mmol, 1.0 equiv.), anhydrous THF (96 mL), and methyl iodide (3.0 mL, 48 mmol, 2.0 equiv.) under argon. The mixture was cooled to 0° C. and treated with sodium hydride (1.92 g, 48 mmol, 2.0 equiv.) in portions. The resulting suspension was stirred for 3 h while the reaction was allowed to return to ambient temperature. Then 100 ml of water was added. The clear solution was concentrated in vacuo to remove the most of THF and was then extracted with ethyl acetate three times. The combined organic phase was washed with 0.5 N hydrochloric acid (50 mL), 5% sodium bicarbonate (50 mL), and brine (50 mL). It was then dried over anhydrous sodium sulfate and concentrated in vacuo to afford a yellow solid, which was purified by recrystallization from ethyl acetate/hexane (20/80, v/v) to afford a nearly colorless solid (9.15 g, 72%). A second recrystallization (ethyl acetate/hexane, 15/60) afforded a white solid (7.92 g), m.p. 115.3-115.8° C. $^1$H NMR (6, CDCl$_3$): 8.22 (s, 1H), 7.78-7.91 (m, 2H), 7.70 (d, J=8.4 Hz, 1H), 7.22-7.45 (m, 5H), 6.99 (s, 1H), 4.50-4.71 (m, 1H), 3.96-4.14 (m, 1H), 3.63-3.77 (m, 1H), 3.51 (s, 4H), 2.59-3.29 (m, 5H), 2.00-2.18 (m, 1H), 1.40 (s, 9H), 1.06 (d, J=6.4 Hz, 3H), 0.96 (d, J=6.4 Hz, 3H). MS 1083 (2MNa)$^+$, 553 (MNa)$^+$, 431 (M-BOC)$^+$ and 589 (AcOM)$^-$. Purity 96% (HPLC).

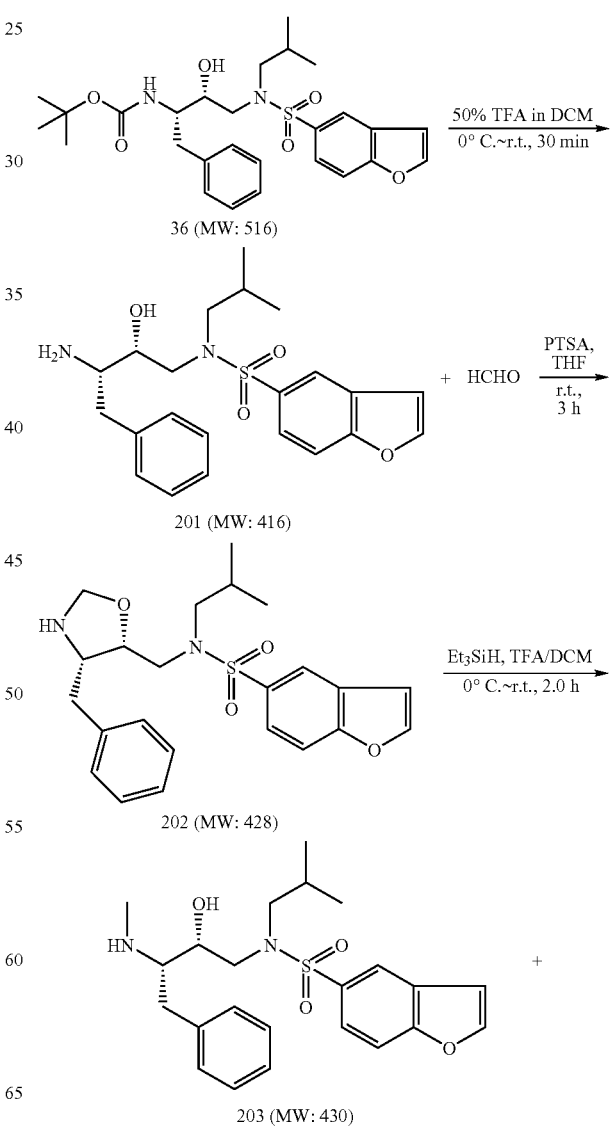

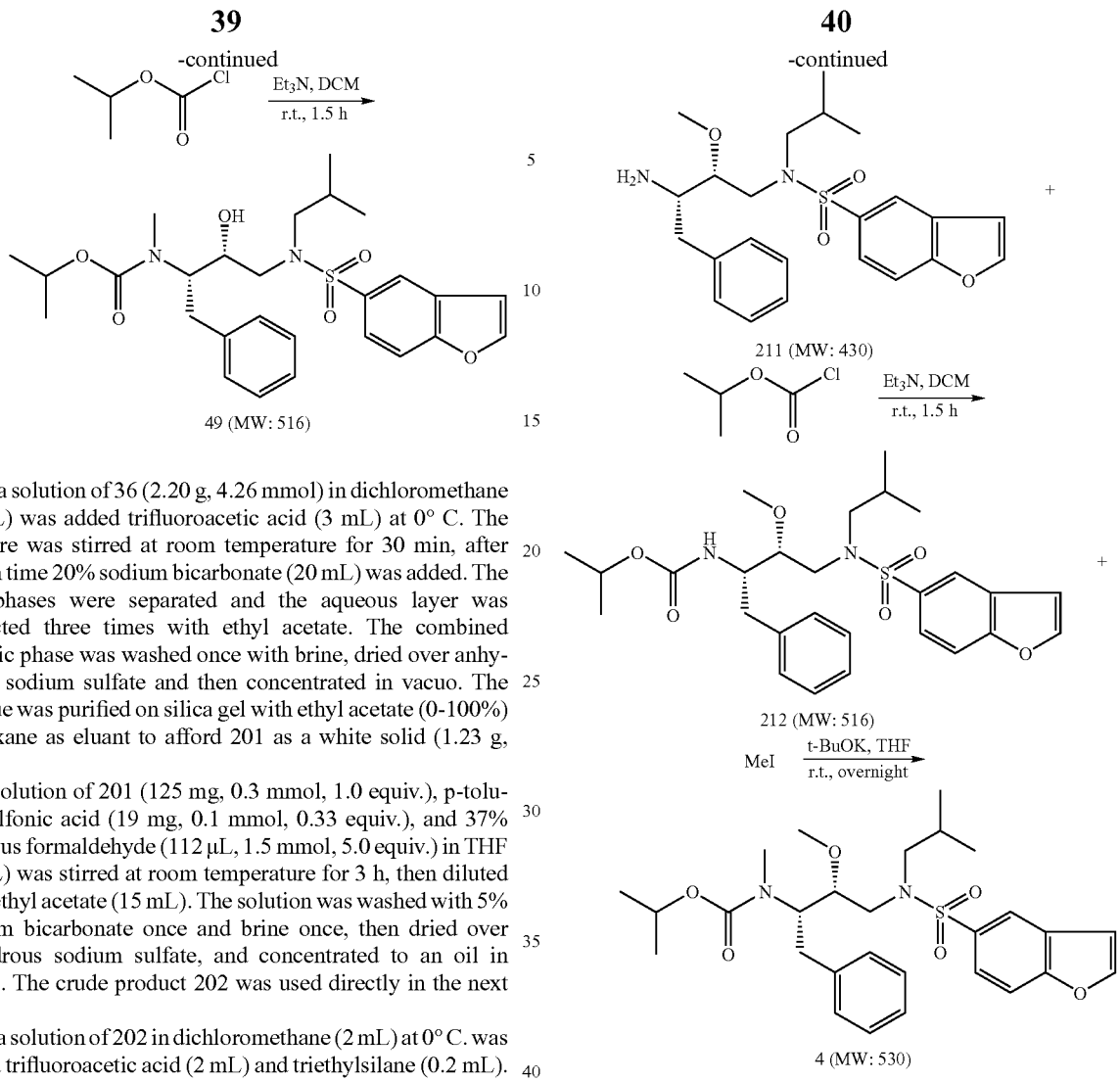

To a solution of 36 (2.20 g, 4.26 mmol) in dichloromethane (6 mL) was added trifluoroacetic acid (3 mL) at 0° C. The mixture was stirred at room temperature for 30 min, after which time 20% sodium bicarbonate (20 mL) was added. The two phases were separated and the aqueous layer was extracted three times with ethyl acetate. The combined organic phase was washed once with brine, dried over anhydrous sodium sulfate and then concentrated in vacuo. The residue was purified on silica gel with ethyl acetate (0-100%) in hexane as eluant to afford 201 as a white solid (1.23 g, 72%).

A solution of 201 (125 mg, 0.3 mmol, 1.0 equiv.), p-toluenesulfonic acid (19 mg, 0.1 mmol, 0.33 equiv.), and 37% aqueous formaldehyde (112 µL, 1.5 mmol, 5.0 equiv.) in THF (3 mL) was stirred at room temperature for 3 h, then diluted with ethyl acetate (15 mL). The solution was washed with 5% sodium bicarbonate once and brine once, then dried over anhydrous sodium sulfate, and concentrated to an oil in vacuo. The crude product 202 was used directly in the next step.

To a solution of 202 in dichloromethane (2 mL) at 0° C. was added trifluoroacetic acid (2 mL) and triethylsilane (0.2 mL). The mixture was stirred at room temperature for 2 h and then quenched with saturated sodium bicarbonate. This solution was extracted three times with ethyl acetate. The combined organic phase was dried over anhydrous sodium sulfate and concentrated to dryness. The crude product 203 was used directly in the next step.

To a solution of 203 in dichloromethane (3 mL) was added triethylamine (84 µL, 0.6 mmol, 2.0 equiv.) and 1.0 M isopropyl chloroformate solution in toluene (0.45 mL, 0.45 mmol, 1.5 equiv.). The mixture was stirred at room temperature for 1.5 h and then the solution was mixed with a small amount of silica gel and evaporated in vacuo to dryness. The residue was purified on silica gel to afford a white solid, 49 (42 mg, 27% overall). MS 517 (MH)$^+$ and 575 (AcOM)$^-$. Purity 99% (HPLC).

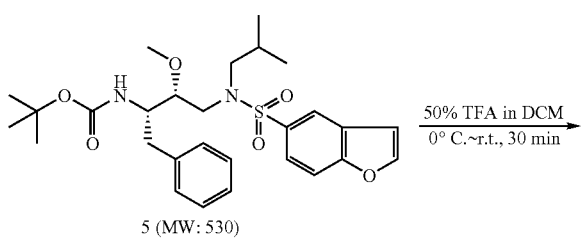

To a solution of 5 (200 mg, 0.377 mmol) in dichloromethane (1 mL) was added trifluoroacetic acid (0.5 mL) at 0° C. The mixture was stirred at room temperature for 30 min, after which time 20% sodium bicarbonate (10 mL) was added. The phases were separated and aqueous layer extracted three times with ethyl acetate. The combined organic phase was washed once with brine, dried over anhydrous sodium sulfate and then concentrated in vacuo. The crude product (211, 105 mg) was used directly in the next step.

To a solution of 211 in dichloromethane (2 mL) was added triethylamine (68 µL, 0.448 mmol, 2.0 equiv.) and 1.0 M isopropyl chloroformate solution in toluene (0.37 mL, 0.366 mmol, 1.5 equiv.). The mixture was stirred at room temperature for 1.5 h and a small amount of silica gel was added. Then the solution was evaporated to dryness in vacuo. The residue was purified on silica gel (0-40% ethyl acetate in hexane) to afford a white solid, 212 (90 mg, 71%). MS 517 (MH)$^+$ and 575 (AcOM)$^-$. Purity>99% (HPLC).

To a solution of 212 (61 mg, 0.118 mmol, 1.0 equiv.) in THF (1 mL) was added potassium tert-butoxide (53 mg, 0.473 mmol, 4.0 equiv.). After the mixture was stirred at room temperature for 30 min, methyl iodide (29 µL, 0.473 mmol, 4.0 equiv.) was added. The reaction was stirred overnight and then quenched with methanol. The solution was mixed with a small amount of silica gel and concentrated to dryness and the residue was purified on silica gel (0-40% ethyl acetate in hexane) to afford 4 (33 mg, 53%). MS 1083 (2MNa)⁺, 531 (MH)⁺ and 567 (MCl)⁻. Purity>99% (HPLC).

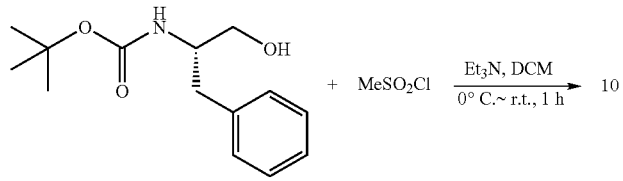

Boc-N-L-phenylalaninol

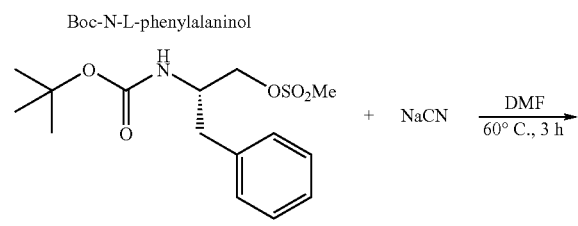

221 (MW: 329)

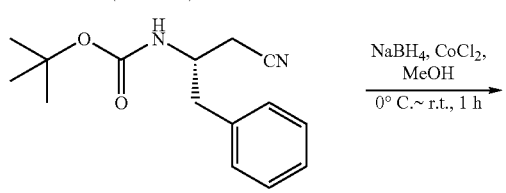

222 (MW: 260)

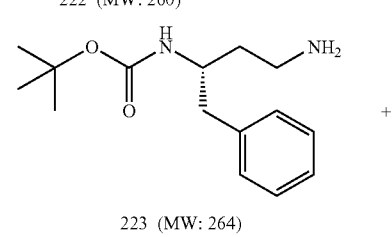

223 (MW: 264)

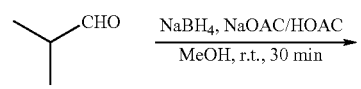

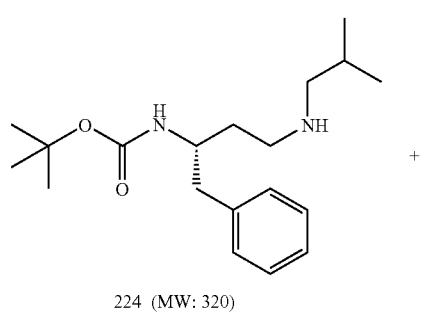

224 (MW: 320)

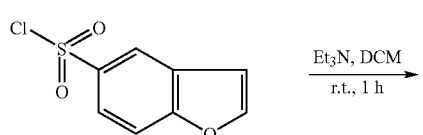

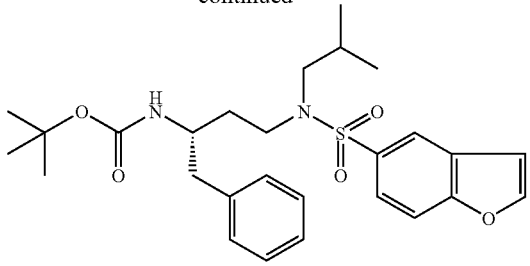

11 (MW: 500)

To an ice-cooled solution of Boc-L-phenylaminol (2.51 g, 10.0 mmol, 1.0 equiv.) in dichloromethane (40 mL) were added triethylamine (2.1 mL, 15.0 mmol, 1.5 equiv.) and methanesulfonyl chloride (1.2 mL, 15 mmol, 1.5 equiv.). The reaction mixture was stirred for 30 min at 0° C. then 30 min at room temperature. The organic phase was washed consecutively with brine, 1M HCl, brine, 5% aqueous NaHCO3, and brine, dried over anhydrous sodium sulfate and concentrated under reduced pressure to afford the mesylate as a yellow oil (221), which was used directly in the next step.

221 was dissolved in DMF (20 mL), and sodium cyanide (1.2 g, 25 mmol, 2.5 equiv.) was added. The reaction mixture was heated to 60° C. and stirred for 3 h. After cooling to room temperature, water (120 mL) was added and the precipitate was collected and washed with water twice and dried in vacuo overnight. The solid was chromatographed (0-50% ethyl acetate in hexane) on silica gel to afford 222 as a white solid (0.6 g, 23% yield for the two steps). 222 (104 mg, 0.4 mmol, 1.0 equiv.) and cobaltous chloride hexahydrate (190 mg, 0.8 mmol, 2.0 equiv.) were dissolved in methanol and sodium borohydride (151 mg, 4.0 mmol, 10 equiv.) was added in portions with stirring at 0° C. Evolution of hydrogen gas and then a black precipitate was observed during the addition. When the addition was complete, stirring was continued for 1 hour at room temperature. Then the reaction was quenched by the addition of 1.0 M aqueous HCl (6 mL). The mixture was stirred until the black precipitate was dissolved. After the removal of methanol in vacuo and unreacted starting material by extraction with ether, the aqueous layer was made alkaline with concentrated ammonium hydroxide and extracted with ethyl acetate three times. The combined organic phase was washed twice with brine, dried over anhydrous sodium sulfate, and concentrated. Crude 223 (79.4 mg) was used directly in the next step.

To a solution of 223 (79 mg, 0.3 mmol, 1.0 equiv.) in methanol (3 mL) were added sodium acetate (54 mg, 0.66 mmol, 2.2 equiv.), acetic acid (38 µL, 0.66 mmol, 2.2 equiv.) and isobutyraldehyde (60 µL, 0.66 mmol, 2.2 equiv.). The mixture was stirred and treated with sodium borohydride (50 mg, 1.32 mmol, 4.4 equiv.). After the reaction solution was stirred for 30 min at room temperature, 20% aqueous NaHCO₃ was added. The reaction mixture was extracted with ethyl acetate three times and the combined organic phase was washed with brine twice, dried over anhydrous sodium sulfate and concentrated in vacuo to afford crude 224 (92 mg), which was used directly in the next step.

To a solution of 224 (45 mg, 0.14 mmol, 1.0 equiv.) in dichloromethane (1.5 mL) was added benzofuran-5-sulfonyl chloride (46 mg, 0.21 mmol, 1.5 equiv.) and triethylamine (39 µL, 0.28 mmol, 2.0 equiv.). The mixture was stirred at room temperature for 1 h and then the solution was mixed with a small amount of silica gel and evaporated in vacuo to dryness. The residue was chromatographed on silica gel to afford 11 as a white solid, (26 mg, 38%). MS 1023 (2MNa)+, 401 (M-Boc)+ and 559 (AcOM)−. Purity>99% (HPLC).

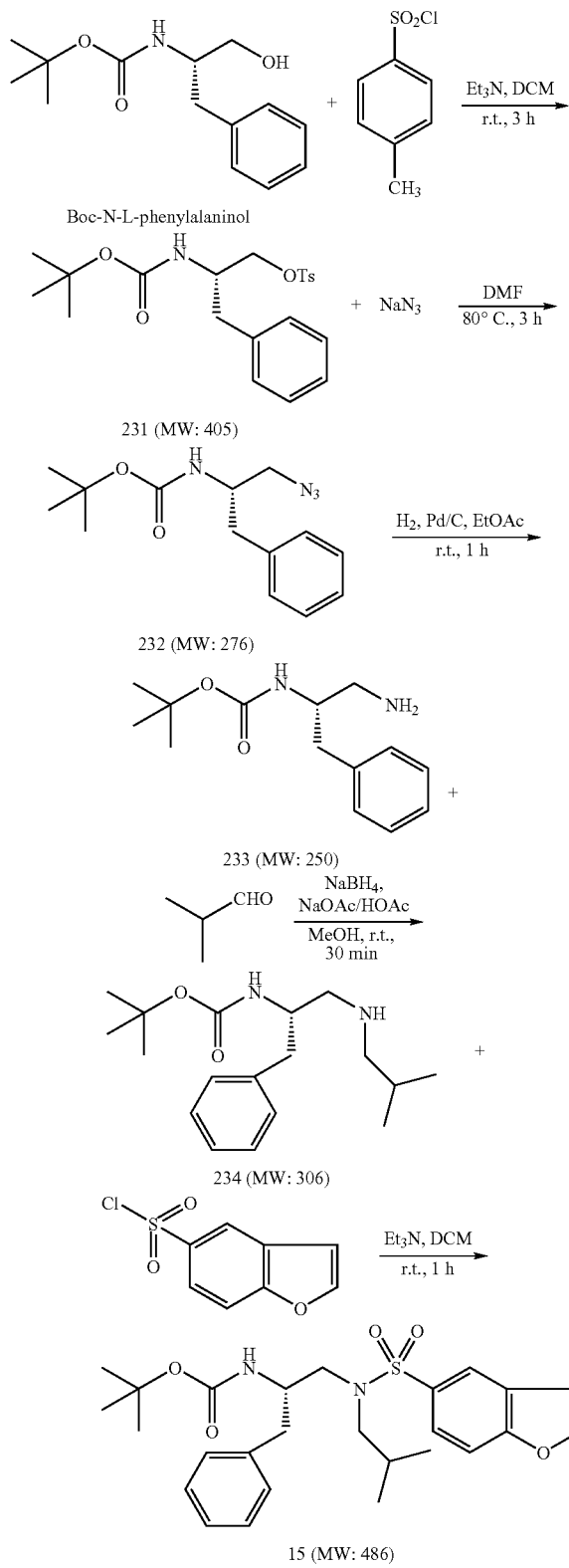

Boc-L-phenylalaminol (1.01 g, 4.0 mmol, 1.0 equiv.) and p-toluenesulfonyl chloride (0.92 g, 4.8 mmol, 1.2 equiv.) were dissolved in dichloromethane (20 mL) and to the solution was added triethylamine (0.84 mL, 6.0 mmol, 1.5 equiv.) at room temperature. The resulting mixture was stirred for 3 h, and then the reaction was quenched with saturated ammonium chloride solution. The phases were separated and the water layer was extracted with ether twice. The combined organic phase was washed once with brine, dried over anhydrous sodium sulfate and concentrated in vacuo. The residue was chromatographed on silica gel (0-20% ethyl acetate in hexane) to afford 231 as a white solid (0.61 g, 38%). Purity 99% (HPLC).

231 (261 mg, 0.64 mmol, 1.0 equiv.) was dissolved in DMF (1.5 mL), and sodium azide (84 mg, 1.28 mmol, 2.0 equiv.) was added. The reaction mixture was heated to 80° C. and stirred for 3 h. After cooling to room temperature, the solution was partitioned between water (5 mL) and ethyl acetate (10 mL). The organic phase was washed with 1N HCl, 5% NaHCO3, and water, dried over anhydrous sodium sulfate and then concentrated in vacuo. The residue was chromatographed on silica gel to afford 232 as a white solid (87 mg, 49%). Purity 99% (HPLC). 232 (87 mg, 0.31 mmol) dissolved in ethyl acetate (3 mL) was hydrogenated at atmospheric pressure for 1 h in the presence of 10% Pd/C (20 mg). The catalyst was removed by filtration through Celite, and the filtrate was concentrated in vacuo to give 233, which was used directly in the next step.

To a solution of 233 in methanol (3 mL) were added sodium acetate (49 mg, 0.60 mmol, 2.0 equiv.), acetic acid (34 μL, 0.60 mmol, 2.0 equiv.) and isobutyraldehyde (55 μL, 0.60 mmol, 2.0 equiv.). The mixture was stirred and treated with sodium borohydride (45 mg, 1.2 mmol, 4.0 equiv.). After 30 min at room temperature, 20% NaHCO3 was added to quench the reaction. The reaction mixture was extracted with ethyl acetate three times and the combined organic phase was washed with brine twice, dried over anhydrous sodium sulfate and concentrated in vacuo to give 234, which was used directly in the next step.

To a solution of 234 in dichloromethane (3 mL) was added benzofuran-5-sulfonyl chloride (97 mg, 0.45 mmol, 1.5 equiv.) and triethylamine (84 μL, 0.60 mmol, 2.0 equiv.). The mixture was stirred at room temperature for 1 h and then the solution was concentrated in vacuo. Preparative TLC (30% ethyl acetate in hexane) afforded 15 as a white solid (14 mg, yield 10% overall). MS 995 (2MNa)+, 509 (MNa)+, 387 (M-Boc)+, 545(AcOM)−, and 485 (M-H)−. Purity 97% (HPLC).

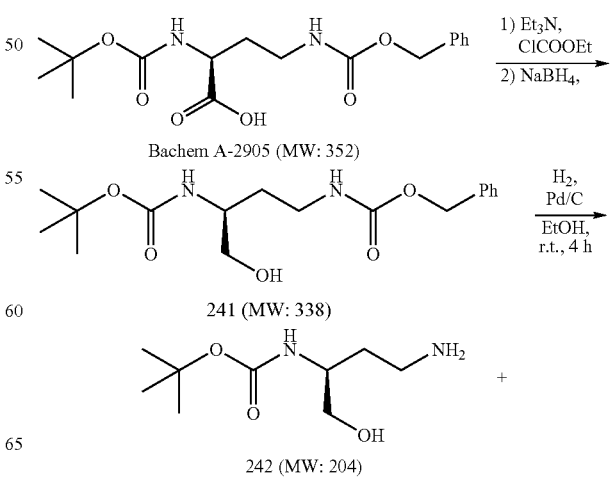

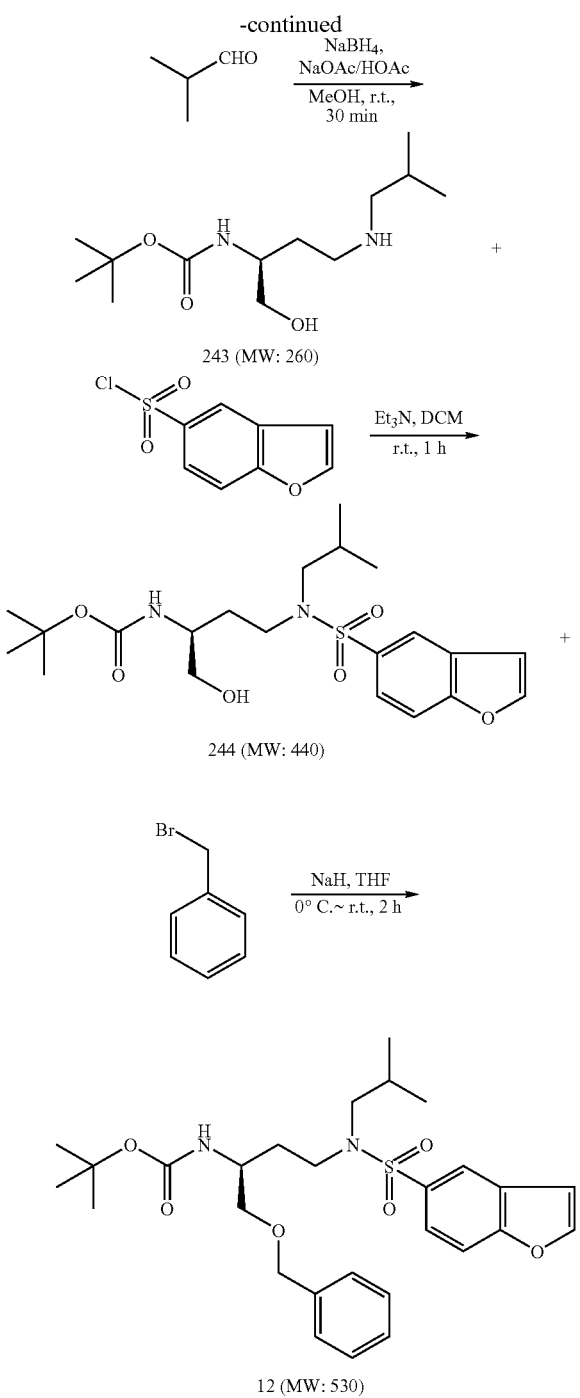

To a solution of 241 (170 mg, 0.5 mmol) in ethanol (5 mL) was added 10% Pd/C (30 mg). A hydrogen balloon was connected to the reaction vessel. After the system was fully flushed with hydrogen, the reaction mixture was stirred at room temperature for 4 h, and then filtered through celite and concentrated in vacuo to give 97 mg of 242, which was used directly in the next step.

To a solution of 242 (45 mg, 0.22 mmol, 1.0 equiv.) in methanol (2 mL) were added sodium acetate (36 mg, 0.44 mmol, 2.0 equiv.), acetic acid (25 μL, 0.44 mmol, 2.0 equiv.) and isobutyraldehyde (40 μL, 0.44 mmol, 2.0 equiv.). The mixture was stirred and treated with sodium borohydride (33 mg, 0.88 mmol, 4.0 equiv.). After the reaction solution was stirred for 30 min at room temperature, 20% NaHCO$_3$ was added. The reaction mixture was extracted with ethyl acetate three times and the combined organic phase was washed with brine twice, dried over anhydrous sodium sulfate and concentrated in vacuo to give 243, which was used directly in the next step.

To a solution of 243 in dichloromethane (2 mL) was added benzofuran-5-sulfonyl chloride (65 mg, 0.30 mmol, 1.5 equiv.) and triethylamine (56 μL, 0.40 mmol, 2.0 equiv.). The mixture was stirred at room temperature for 1 h and then the solution was concentrated in vacuo. The residue was chromatographed on silica gel to afford 244 as a white solid (39 mg, 38% for the three steps). MS 903 (2MNa)$^+$, 463 (MNa)$^+$, 341 (M-Boc)$^+$ and 499 (AcOM)$^-$. Purity>99% (HPLC).

To a solution of 244 (36 mg, 0.082 mmol, 1.0 equiv.) in THF (1 mL) was added benzyl bromide (39 μL, 0.327 mmol, 4.0 equiv.) and sodium hydride (13 mg, 0.327 mmol, 4.0 equiv.) at 0° C. The mixture was stirred for 2 h while the reaction temperature was allowed to gradually return to ambient temperature. Then the reaction was quenched with methanol. The solution was mixed with a small amount of silica gel and concentrated in vacuo and the residue was chromatographed on silica gel (0-50% ethyl acetate in hexane) to afford a white solid, 12 (22 mg, 51%). MS 1083 (2MNa)$^+$, 553 (MNa)$^+$, 431 (M-Boc)$^+$ and 589 (MOAc)$^-$. Purity>99% (HPLC).

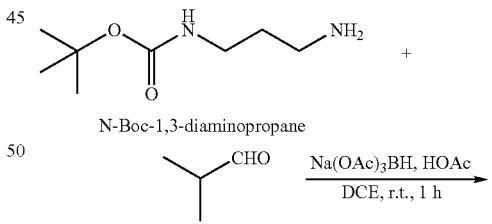

N-Boc-1,3-diaminopropane

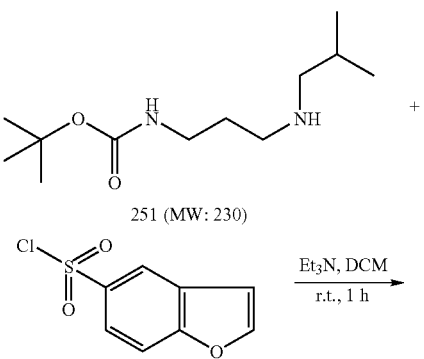

251 (MW: 230)

Boc-L-Dab(Z)-OH.DCHA (534 mg, 1.0 mmol, 1.0 equiv.) was dissolved in THF (6 mL), cooled to 0° C., and treated with triethylamine (210 μL, 1.5 mmol, 1.5 equiv.) and ethyl chloroformate (114 μL, 1.2 mmol, 1.2 equiv.). The resulting mixture was stirred at 0° C. for 30 min and filtered. The filtrate was added dropwise to a slurry of sodium borohydride (190 mg, 5.0 mmol, 5.0 equiv.) in water (6 mL) at 0° C. After 4 h, the mixture was diluted with brine and extracted with ethyl acetate. The combined organic phase was dried over anhydrous sodium sulfate and concentrated in vacuo. The residue was chromatographed on silica gel using 0-75% ethyl acetate/ dichloromethane as eluant to afford 241 as a white solid (170 mg, 50%). Purity 99% (HPLC).

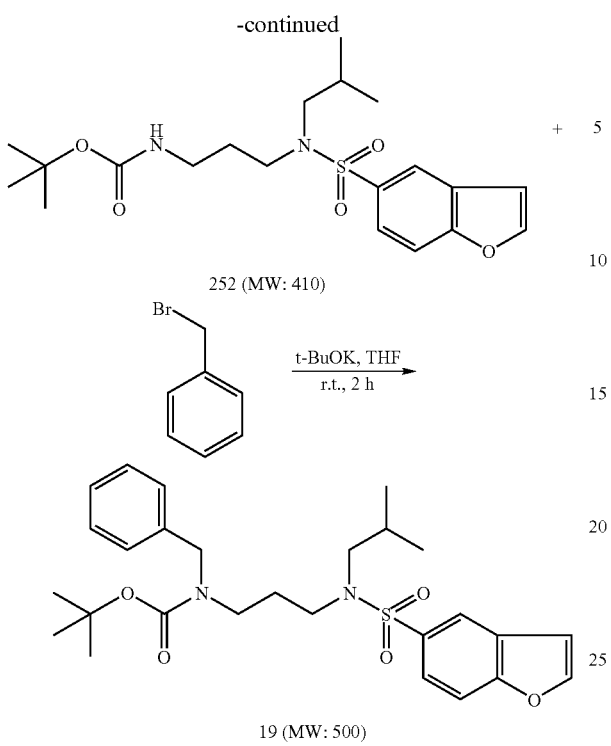

252 (MW: 410)

19 (MW: 500)

To a solution of N-Boc-1,3-diaminopropane (6.97 g, 40 mmol, 1.0 equiv.) in anhydrous 1,2-dichloroethane (160 mL) was added isobutyraldehyde (3.03 g, 42 mmol, 1.05 equiv.) and acetic acid (2.3 mL, 40 mmol, 1.0 equiv.). The solution was stirred for 10 min, and then was treated with sodium triacetoxyborohydride (12.72 g, 60 mmol, 1.5 equiv.). The resulting mixture was stirred for 1 h and then the reaction was quenched with 20% aqueous NaHCO$_3$ (100 mL) and ethyl acetate (200 mL). The layers were separated and the organic phase was washed twice with brine, dried over anhydrous Na$_2$SO$_4$, and concentrated in vacuo to afford crude 251, which was used directly in the next step.

To a solution of 251 (40 mmol, 1.0 equiv.) in dichloromethane (200 mL) was added benzofuran-5-sulfonyl chloride (10.4 g, 48 mmol, 1.2 equiv.) and triethylamine (8.4 mL, 60 mmol, 1.5 equiv.). The mixture was stirred at room temperature for 2 h and then the reaction was quenched by the addition of 1M HCl solution (100 mL) and ethyl acetate (200 mL). The two phases was separated and the organic layer was washed with brine twice, dried over anhydrous Na$_2$SO$_4$, and concentrated in vacuo. The residue was purified on silica gel with ethyl acetate/hexane (1/3) as eluant to afford a colorless oil, 252 (5.62 g, 34% overall). MS 433 (MNa)$^+$, 311 (M-Boc)$^+$ and 469 (AcOM)$^-$. Purity>99% (HPLC).

To a solution of 252 (5.6 g, 13.7 mmol, 1.0 equiv) in anhydrous THF (70 mL) was added potassium tert-butoxide (3.07 g, 27.3 mmol, 2.0 equiv.) immediately followed by benzyl bromide (2.4 mL, 20.5 mmol, 1.5 equiv.). The resulting mixture was stirred at room temperature for 1 h, after which time the reaction was quenched by the addition of 1M HCl solution and ether. The two phases were separated and the water layer was extracted twice with ether. The combined organic phase was washed twice with brine, dried over anhydrous Na$_2$SO$_4$ and concentrated in vacuo. The residue was purified on silica gel with ethyl acetate/hexane (1/6) as eluant to afford 19 as a colorless oil (6.5 g, 95%). $^1$H NMR (δ, CDCl$_3$): 8.19 (s, 1H), 7.86 (s, 1H), 7.81 (d, J=8.7 Hz, 1H), 7.69 (d, J=8.7 Hz, 1H), 7.22-7.45 (m, 5H), 6.98 (s, 1H), 4.50 (s, 2H), 3.05-3.30 (m, 4H), 2.96 (d, J=7.4 Hz, 2H), 1.75-1.94 (m, 3H), 1.55 (s, 9H), 0.99 (d, J=6.6 Hz, 6H). MS 523 (MNa)$^+$, and 401 (M-Boc). Purity>99% (HPLC).

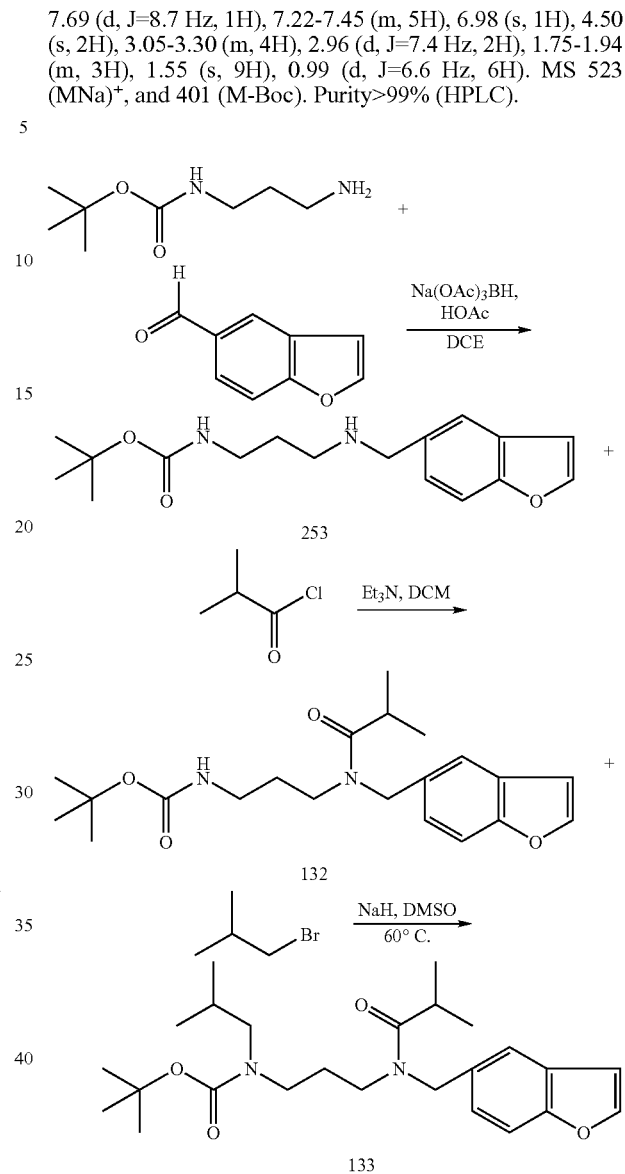

To a solution of benzofuran-5-carbaldehyde (146 mg, 1.0 mmol, 1.0 equiv.) in anhydrous 1,2-dichloroethane (5 mL) was added N-Boc-1,3-diaminopropane (192 μL, 1.1 mmol, 1.1 equiv.) and acetic acid (57 μL, 1.0 mmol, 1.0 equiv.). The solution was stirred for 10 min, and then was treated with sodium triacetoxyborohydride (297 mg, 1.4 mmol, 1.4 equiv.). The resulting mixture was stirred for 3 h at room temperature and then the reaction was quenched with the addition of saturated aqueous NaHCO$_3$ solution. The aqueous layer was extracted with ethyl acetate three times and the combined organic phase was washed twice with brine, dried over anhydrous Na$_2$SO$_4$, and concentrated in vacuo to afford crude 253 (287 mg), which was used directly in the next step.

To a solution of 253 (96 mg, 0.32 mmol, 1.0 equiv.) in dichloromethane (1 mL) was added isobutyryl chloride (34 μL, 0.32 mmol, 1.0 equiv.) and triethylamine (49 μL, 0.35 mmol, 1.1 equiv.). The mixture was stirred at room temperature for 1 h and then the reaction solution was transferred via syringe onto a preparative silica gel TLC plate. The plate was eluted with 1:3 ethyl acetate/hexane to give 105 mg (88%) 132, MS 771 (2MNa)$^+$, 397 (MNa)$^+$, 375 (MH)$^+$, 275 (M-Boc)$^+$. HPLC purity>99%.

132 (38 mg, 0.1 mmol, 1.0 equiv) and sodium hydride (60% dispersion in mineral oil, 8 mg, 0.2 mmol, 2.0 equiv.) were dissolved in anhydrous DMSO (0.5 mL). The solution was stirred at room temperature for 5 min and then was treated with isobutyl bromide (24 μL, 0.22 mmol, 2.2 equiv.). The mixture was heated to 60° C. and stirred for 1.5 h and then returned to room temperature. An additional portion of sodium hydride (8 mg, 0.2 mmol, 2.0 equiv.) was introduced and 5 minutes later an additional portion of isobutyl bromide (24 μL, 0.22 mmol, 2.2 equiv.). The resulting mixture was heated to 60° C. and stirred for an additional 1.5 h and the reaction then quenched with methanol. The final solution was transferred via syringe onto a preparative silica gel TLC plate. The plate was eluted with 1:4 ethyl acetate/hexane to give 15 mg (35%) 133. MS 883 (2MNa)$^+$, 453 (MNa)$^+$, 431 (MH)$^+$ and 331 (M-Boc)$^+$. HPLC purity>99%.

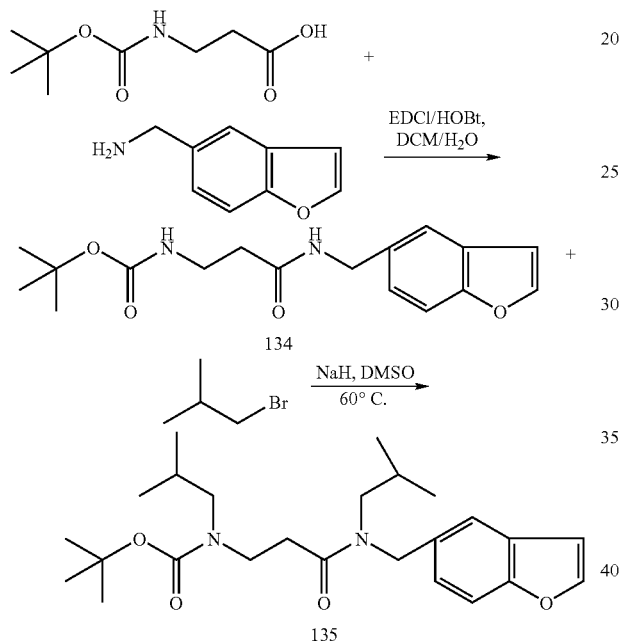

To a solution of benzofuran-5-ylmethylamine (147 mg, 1.0 mmol, 1.0 equiv.) in dichloromethane (10 mL) were added sequentially water (10 mL), Boc-β-Ala-OH (208 mg, 1.1 mmol, 1.1 equiv.) and HOBT (149 mg, 1.1 mmol, 1.1 equiv.). The mixture was then cooled in an ice bath to 0-5° C., and N-(3-Dimethylaminopropyl)-N'-ethylcarbodiimide hydrochloride (EDCI) (211 mg, 1.1 mmol, 1.1 equiv.) was added. The resulting mixture was then stirred overnight at room temperature. The reaction was quenched with saturated aqueous NaHCO$_3$ solution. The aqueous phase was extracted with ethyl acetate three times and the combined organic phase was dried over anhydrous Na$_2$SO$_4$, and concentrated in vacuo. The residue was purified using medium pressure chromatography (ethyl acetate/hexane gradient, 0-100%) to afford 258 mg (81%) 134 as a white solid, MS 659 (2MNa)$^+$, 341 (MNa)$^+$, 319 (MH)$^+$, and 377. HPLC purity>99%.

134 (48 mg, 0.15 mmol, 1.0 equiv) and sodium hydride (60% dispersion in mineral oil, 12 mg, 0.3 mmol, 2.0 equiv.) were added to anhydrous DMSO (0.7 mL). The solution was stirred at room temperature for 10 min and then treated with isobutyl bromide (33 μL, 0.30 mmol, 2.0 equiv.). The mixture was then heated to 60° C. and stirred for 1 h and then returned to room temperature. An additional portion of sodium hydride (12 mg, 0.3 mmol, 2.0 equiv.) was introduced and 5 minutes later an additional portion of isobutyl bromide (33 μL, 0.30 mmol, 2.0 equiv.). The resulting mixture was heated to 60° C. and stirred for 1 h and then returned to room temperature and quenched with methanol. The final solution was transferred onto a preparative silica gel TLC plate via syringe. The plate was eluted with 1:3 ethyl acetate/hexane to give 3.0 mg 135 (5%). MS 883 (2MNa)$^+$, 453 (MNa)$^+$, 431 (MH)$^+$ and 331 (M-Boc)$^+$. HPLC purity>99%.

Variations, modifications, and other implementations of what is described herein will occur to those of ordinary skill in the art without departing from the spirit and the scope of the technology. Accordingly, the technology is not to be limited only to the preceding illustrative descriptions.

FIG. 1 provides representative examples of compounds that are active for inhibiting cytochrome p450 enzymes. All of the compounds shown have a Ki that is better than 100 nM.

What is claimed is:

1. A method of inhibiting cytochrome P450 monooxygenase comprising administering to a patient a compound represented by a formula:

X-A-B—X' wherein:

X is selected from the group consisting of alkyl, aryl, aralkyl, heteroaryl, and heteroaralkyl, wherein X contains from 1 to 12 carbon atoms and, when X is heteroaryl or heteroaralkyl, X contains from 1 to 3 heteroatoms independently selected from the group consisting of O, S, and N, A is —OCON(R2)-, —S(O)$_n$N(R2)-, —CON(R2)-, —COCO(NR2)-, —N(R2)CON(R2)-, —N(R2)S(O)$_n$(R2)-, N(R2)CO or —N(R2)COO—;

B is —(CG$_1$G$_2$)$_m$- , wherein m is 2-6 and wherein G$_1$ and G$_2$ are the same or different and wherein each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl wherein each optional substitution independently is selected from the group consisting of alkyl , halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and wherein G$_1$ and G$_2$, together with the atoms to which they are attached, optionally may form a 3-7-membered carbocyclic or heterocyclic ring containing up to three heteroatoms selected from the group consisting of N, S and O, and wherein said ring optionally may be substituted with up to 3 R7 moieties, X' is

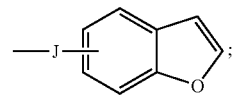

wherein J is selected from:
—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$-N(D)-(R8)$_q$-, or —CO$_n$—N(D)-(R8)$_q$-, wherein D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, wherein D optionally is substituted by alkyl, halo, nitro, cyano, O-alkyl, or S-alkyl;

wherein R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein each R2 is independently selected from the group consisting of H, C1-C12 alkyl, C3-C8 cycloalkyl, aryl, aralkyl, heteroaryl, heteroaralkyl, and heterocycloalkyl each further optionally substituted with one or more substituents selected from the group consisting of C2-C6 alkenyl, C2-C6 alkynyl, C3-C8 cycloalkyl, C5-C8 cycloalkenyl, heterocyclo; halo, OR, ROH, R-halo, NO2, CN, COnR, CON(R)2, C(S)R, C(S)N(R)2, SOnN(R)2, SR, SOnR, N(R)2, N(R)COnR, NRS(O)nR, NRC[=N(R)]N(R)2, N(R)N(R)COnR, NRPOnN(R)2, NRPOnOR, oxo, =N—OR, =N—N(R)2, =NR, =NNRC(O)N(R)2, =NNRCOnR, =NNRS(O)nN(R)2, and =NNRS(O)n(R);

or each R2 is independently selected from the group consisting of C1-C6 alkyl; substituted by aryl or heteroaryl; which groups optionally are substituted with one or more substituents selected from the group consisting of halo, OR, ROH, R-halo, NO2, CN, COnR, CON(R)2, C(S)R, C(S)N(R)2, SOnN(R)2, SR, SOnR, N(R)2, N(R)COnR, NRS(O)nR, NRC[=N(R)]N(R)2, N(R)N(R)COnR, NRPOnN(R)2, NRPOnOR;

R3 is C2-C6 alkenyl, C2-C6 alkynyl, C3-C8 cycloalkyl, C5-C8 cycloalkenyl, or heterocyclo; which groups optionally are substituted with one or more substituents selected from the group consisting of halo, OR2, R2-OH, R2-halo, NO2, CN, COnR2, C(O)N(R2)2, C(O)N(R2)N(R2)2, C(S)R2, C(S)N(R2)2, S(O)nN(R2)2, SR2, SOnR2, N(R)2, N(R2)COnR2, NR2S(O)nR2, NR2C[=(R2)]N(R2)2, N(R2)N(R2)COnR2, oxo, =N—OR2, =N—N(R2)2, =NR2, =NNRC(O)N(R2)2, =NNR2C(O)nR2, =NNR2S(O)nN(R2)2, and =NNR2S(O)n(R2);

R6 is aryl or heteroaryl, wherein said aryl or heteroaryl optionally are substituted with one or more groups selected from the group consisting of aryl, heteroaryl, R2, R3, halo, OR2, R2OH, R2-halo, NO2, CN, COnR2, C(O)N(R2)2, C(O)N(R2)N(R2)2, C(S)R2, C(S)N(R2)2, S(O)nN(R2)2, SR2, SOnR2, N(R)2, N(R2)COnR2, NR2S(O)nR2, NR2C[=N(R2)]N(R2)2, N(R2)N(R2)COnR2, OC(O)R2, OC(S)R2, OC(O)N(R2)2, and OC(S)N(R2)2;

R7 is H, oxo, C1-C12 alkyl; C3-C8 cycloalkyl, aryl, aralkyl, heteroaryl, heteroaralkyl, or heterocycloalkyl, each further optionally substituted with one or more substituents selected from the group consisting of C2-C6 alkenyl, C2-C6 alkynyl, C3-C8 cycloalkyl, C5-C8 cycloalkenyl, heterocyclo; halo, OR, ROH, R-halo, NO2, CN, COnR, CON(R)2, C(S)R, C(S)N(R)2, SOnN(R)2, SR, SOnR, N(R)2, N(R)COnR, NRS(O)nR, NRC[=N(R)]N(R)2, N(R)N(R)COnR, NRPOnN(R)2, NRPOnOR, oxo, =N—OR, =N—N(R)2, =NR, =NNRC(O)N(R)2, =NNRCOnR, =NNRS(O)nN(R)2, and =NNRS(O)n(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein n =1-2, and wherein q =0-1, provided that: when X is a 5-7 membered non-aromatic monocyclic heterocycle, optionally fused or bridged with one or more 3-7 membered non-aromatic monocyclic heterocycle to form a polycyclic system, wherein any of said heterocyclic ring systems contains one or more heteroatoms selected from O, N, S, and P, and when B is

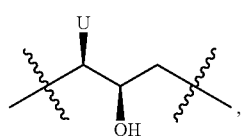

wherein U is selected from optionally substituted alkyl, optionally substituted alkenyl, optionally substituted alkynyl, optionally substituted aryl, optionally substituted cycloalkyl, or optionally substituted aralkyl, then J cannot be —N(D)-SOn- or —N(D)-COn-.

2. The method according to claim 1 wherein X optionally is substituted with one or more substituents selected from the group consisting of halo, OR, ROH, R-halo, CN, $CO_nR$, $CON(R)_2$, $SO_nN(R)_2$, SR, $SO_nR$, $N(R)_2$, $N(R)CO_nR$, $NRS(O)_nR$, oxo, and =N—OR.

3. The method according to claim 1 wherein X optionally is substituted with one or more substituents selected from the group consisting of halo, OR, $CO_nR$, $CON(R)_2$, $SO_nN(R)_2$, $SO_nR$, $N(R)_2$, $N(R)CO_nR$, and oxo.

4. The method according to claim 1 wherein $G_1$ and $G_2$ are the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl.

5. The method according to claim 1 wherein $G_1$ and $G_2$ do not form a ring.

6. The method according to claim 1 wherein at least one $G_1$ and at least one $G_2$ form a ring.

7. The method according to claim 1 wherein $G_1$ and $G_2$ are different.

8. The method according to claim 1 wherein neither $G_1$ nor $G_2$ is OH.

9. The method according to claim 1 wherein G1 and G2 are selected from the group consisting of H, O-alkyl, alkyl, optionally substituted aryl and optionally substituted aralkyl.

10. The method according to claim 1, wherein J is

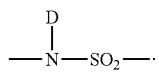

11. The method according to claim 1, wherein J is

12. The method according to claim 1, wherein J is —N(D)-(R8)$_q$-.

13. The method according to claim 1, wherein J is —SO$_n$—N(D)-(R8)$_q$-.

14. The method according to claim 1 wherein J is —CO$_n$—N(D)-(R8)$_q$-.

15. The method according to claim 1 wherein D is selected from the group consisting of hydrogen, alkyl, cycloalkyl, cycloalkylalkyl, aryl, heteroaryl, heteroaralkyl and aralkyl, wherein D optionally is substituted by alkyl, halo, nitro, cyano, O-alkyl, or S-alkyl.

16. The method according to claim 15, wherein D optionally is substituted by alkyl, halo, or O-alkyl.

17. The method according to claim 1, wherein D is selected from the group consisting of hydrogen, alkyl, heteroaralkyl and aralkyl, wherein D optionally is substituted by alkyl, halo, nitro, cyano, O-alkyl, and S-alkyl.

18. The method according to claim 1, wherein the cytochrome P450 monooxygenase is CYP3A4 or CYP3A5.

19. The method according to claim 1, wherein said compound does not inhibit HIV protease.

20. The method according to claim 1, wherein the patient is suffering from chronic pain, depression, epilepsy, psychosis, inflammation, cancer, cardiovascular disease, diabetes, and/or infection.

21. The method according to claim 20, wherein the patient is suffering from HCV or HIV infection.

22. The method according to claim 1, wherein the compound is administered prior to, and/or substantially contemporaneously with, a drug wherein efficacy of said drug is compromised due to degradation by cytochrome P450 monooxygenase.

23. The method according to claim 22, wherein the compound is administered at least 30 minutes, at least 1 hour, at least 2 hours, or at least 12 hours prior to administration of said drug.

24. A method of inhibiting cytochrome P450 monooxygenase comprising administering to a patient a compound represented by a formula:

X-A-B—X' wherein:
X is selected from the group consisting of alkyl, aryl, aralkyl, heteroaryl, and heteroaralkyl, wherein X contains from 1 to 12 carbon atoms and, when X is heteroaryl or heteroaralkyl, X contains from 1 to 3 heteroatoms independently selected from the group consisting of O, S, and N;

A is selected from the group consisting of a bond, —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, wherein m is 0-6 and wherein G$_1$ and G$_2$ are the same or different and wherein each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl wherein each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and wherein G$_1$ and G$_2$, together with the atoms to which they are attached, optionally may form a 3-7-membered carbocyclic or heterocyclic ring containing up to three heteroatoms selected from the group consisting of N, S and O, and wherein said ring optionally may be substituted with up to 3 R7 moieties, X' is

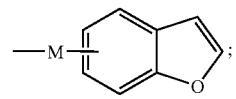

wherein M is selected from the group consisting of: a bond, OC(R8)$_q$, —CO—, —SO$_n$—, —O—, —O—CO—, —N(D)-SO$_n$—, —N(D)-CO$_n$—, —N(D)-(R8)$_q$-, —N(CO-D)-(R8)$_q$-, —N(SO$_n$-D)-(R8)$_q$, —SO$_n$—N(D)-(R8)$_q$-, or —CO$_n$—N(D)-(R8)$_q$-, wherein M can be linked in either orientation with respect to the benzofuran ring, wherein D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, and N(R2)-aralkyl, wherein D optionally is substituted by alkyl, halo, nitro, cyano, O-alkyl, or S-alkyl;

wherein R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein each R2 is independently selected from the group consisting of H, C$_1$-C$_{12}$ alkyl, C$_3$-C$_8$ cycloalkyl, aryl, aralkyl, heteroaryl, heteroaralkyl, and heterocycloalkyl each further optionally substituted with one or more substituents selected from the group consisting of C$_2$-C$_6$ alkenyl, C$_2$-C$_6$ alkynyl, C$_3$-C$_8$ cycloalkyl, C$_5$-C$_8$ cycloalkenyl, heterocyclo, halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR, oxo, ═N—OR, ═N—N(R)$_2$, ═NR, ═NNRC(O)N(R)$_2$, ═NNRCO$_n$R, ═NNRS(O)$_n$N(R)$_2$, and ═NNRS(O)$_n$(R);

or each R2 is independently selected from the group consisting of C$_1$-C$_6$ alkyl; substituted by aryl or heteroaryl; which groups optionally are substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR;

R3 is C$_2$-C$_6$ alkenyl, C$_2$-C$_6$ alkynyl, C$_3$-C$_8$ cycloalkyl, C$_5$-C$_8$ cycloalkenyl, or heterocyclo; which groups optionally are substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[═N(R2)]N(R2)$_2$, N(R2)N(R2)CO$_n$R2, oxo, ═N—OR2, ═N—N(R2)$_2$, ═NR2, ═NNRC(O)N(R2)$_2$, ═NNR2C(O)$_n$R2, ═NNR2S(O)$_n$N(R2)$_2$, and ═NNR2S(O)$_n$(R2);

R6 is aryl or heteroaryl, wherein said aryl or heteroaryl optionally is substituted with one or more groups selected from the group consisting of aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, OC(O)R2, OC(S)R2, OC(O)N(R2)$_2$, and OC(S)N(R2)$_2$;

R7 is H, oxo, C$_1$-C$_{12}$ alkyl; C$_3$-C$_8$ cycloalkyl, aryl, aralkyl, heteroaryl, heteroaralkyl, or heterocycloalkyl, each further optionally substituted with one or more substituents selected from the group consisting of C$_2$-C$_6$ alkenyl, C$_2$-C$_6$ alkynyl, C$_3$-C$_8$ cycloalkyl, C$_5$-C$_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein n =1-2, and q=0-1, wherein the benzene ring of the benzofuran moiety optionally is substituted by up to three substituents independently selected from the group consisting of R2, halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, and NRPO$_n$OR, wherein said up to three substituents do not form a ring between any adjacent carbon atoms of said benzene ring, and with the proviso that said compound does not contain a basic aliphatic amine function and does not contain a carboxylic acid group, and provided that: when X is a 5-7 membered non-aromatic monocyclic heterocycle, optionally fused or bridged with one or more 3-7 membered non-aromatic monocyclic heterocycle to form a polycyclic system, wherein any of said heterocyclic ring systems contains one or more heteroatoms selected from O, N, S, and P, and when B is

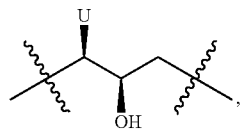

wherein U is selected from optionally substituted alkyl, optionally substituted alkenyl, optionally substituted alkynyl, optionally substituted aryl, optionally substituted cycloalkyl, or optionally substituted aralkyl, then M cannot be —N(D)-SO$_n$— or —N(D)-CO$_n$.

25. A method of inhibiting cytochrome P450 monooxygenase comprising administering to a patient a compound represented by a formula:

X-A-B—X' wherein:

X is selected from the group consisting of alkyl, aryl, aralkyl, heteroaryl, and heteroaralkyl, wherein X contains from 1 to 12 carbon atoms and, when X is heteroaryl or heteroaralkyl, X contains from 1 to 3 heteroatoms independently selected from the group consisting of O, S, and N, A is —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, wherein m is 3 and wherein G$_1$ and G$_2$ are the same or different and wherein each G$_1$ and G$_2$ are the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl, wherein each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and wherein G$_1$ and G$_2$, together with the atoms to which they are attached, optionally may form a 3-7-membered carbocyclic or heterocyclic ring containing up to three heteroatoms selected from the group consisting of N, S and O, and wherein said ring optionally may be substituted with up to 3 R7 moieties, X' is

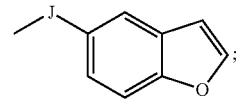

wherein J is selected from:
—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-, wherein D is selected from the group consisting of hydrogen, alkyl, cycloalkyl, cycloalkylalkyl, aryl, heteroaryl, heteroaralkyl and aralkyl, wherein D optionally is substituted by alkyl, halo, nitro, cyano, O-alkyl, or S-alkyl;

wherein R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein each R2 is independently selected from the group consisting of H, C1-C12alkyl, C3-C8cycloalkyl, aryl, aralkyl, heteroaryl, heteroaralkyl, and heterocycloalkyl each further optionally substituted with one or more substituents selected from the group consisting of C2-C6alkenyl, C2-C6alkynyl, C3-C8cycloalkyl, C5-C8cycloalkenyl, heterocyclo; halo, OR, ROH, R -halo, NO2, CN, COnR, CON(R)2, C(S)R, C(S)N(R)2, SOnN(R)2, SR, SOnR, N(R)2, N(R)COnR, NRS(O)nR, NRC[=N(R)]N(R)2, N(R)N(R)COnR, NRPOnN(R)2, NRPOnOR, oxo, =N—OR, =N—N(R)2, =NR, =NNRC(O)N(R)2, =NNRCOnR, =NNRS(O)nN(R)2, and =NNRS(O)n(R);

or each R2 is independently selected from the group consisting of C1-C6alkyl;

substituted by aryl or heteroaryl; which groups optionally are substituted with one or more substituents selected from the group consisting of halo, OR, ROH, R-halo, NO2, CN, COnR, CON(R)2, C(S)R, C(S)N(R)2, SOnN (R)2, SR, SOnR, N(R)2, N(R)COnR, NRS(O)nR, NRC[=N(R)]N(R)2, N(R)N(R)COnR, NRPOnN(R)2, NRPOnOR;

R3 is C2-C6alkenyl, C2-C6alkynyl, C3-C8cycloalkyl, C5-C8cycloalkenyl, or heterocyclo; which groups optionally are substituted with one or more substituents selected from the group consisting of halo, OR2, R2-OH, R2-halo, NO2, CN, COnR2, C(O)N(R2)2, C(O)N(R2)N(R2)2, C(S)R2, C(S)N(R2)2, S(O)nN(R2)2, SR2, SOnR2, N(R)2, N(R2)COnR2, NR2S(O)nR2, NR2C[=N(R2)]N(R2)2, N(R2)N(R2)COnR2, oxo, =N—OR2, =N—N(R2)2, =NR2, =NNRC(O)N(R2)2, =NNR2C(O)nR2, =NNR2S(O)nN(R2)2, and =NNR2S(O)n(R2);

R6 is aryl or heteroaryl, wherein said aryl or heteroaryl optionally are substituted with one or more groups selected from the group consisting of aryl, heteroaryl, R2, R3, halo, OR2, R2OH, R2-halo, NO2, CN, COnR2, C(O)N(R2)2, C(O)N(R2)N(R2)2, C(S)R2, C(S)N(R2)2, S(O)nN(R2)2, SR2, SOnR2, N(R)2, N(R2)COnR2, NR2S(O)nR2, NR2C[=N(R2)]N(R2)2, N(R2)N(R2)COnR2, OC(O)R2, OC(S)R2, OC(O)N(R2)2, and OC(S)N(R2)2;

R7 is H, oxo, C1-C12alkyl; C3-C8cycloalkyl, aryl, aralkyl, heteroaryl, heteroaralkyl, or heterocycloalkyl, each further optionally substituted with one or more substituents selected from the group consisting of C2-C6alkenyl, C2-C6alkynyl, C3-C8cycloalkyl, C5-C8cycloalkenyl, heterocyclo; halo, OR, ROH, R-halo, NO2, CN, COnR, CON(R)2, C(S)R, C(S)N(R)2, SOnN(R)2, SR, SOnR, N(R)2, N(R)COnR, NRS(O)nR, NRC[=N(R)]N(R)2, N(R)N(R)COnR, NRPOnN(R)2, NRPOnOR, oxo, =N—OR, =N—N(R)2, =NR, =NNRC(O)N(R)2, =NNRCOnR, =NNRS(O)nN(R)2, and =NNRS(O)n(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein n=1-2, and wherein q=0-1, provided that: when X is a 5-7 membered non-aromatic monocyclic heterocycle, optionally fused or bridged with one or more 3-7 membered non-aromatic monocyclic heterocycle to form a polycyclic system, wherein any of said heterocyclic ring systems contains one or more heteroatoms selected from O, N, S, and P, and when B is

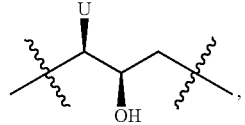

wherein U is selected from optionally substituted alkyl, optionally substituted alkenyl, optionally substituted alkynyl, optionally substituted aryl, optionally substituted cycloalkyl, or optionally substituted aralkyl, then J cannot be —N(D)-SOn- or —N(D)-COn-.

* * * * *

UNITED STATES PATENT AND TRADEMARK OFFICE
CERTIFICATE OF CORRECTION

| | | |
|---|---|---|
| PATENT NO. | : 8,048,871 B2 | Page 1 of 1 |
| APPLICATION NO. | : 11/841157 | |
| DATED | : November 1, 2011 | |
| INVENTOR(S) | : Eissenstat et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this
Thirteenth Day of March, 2012

David J. Kappos
*Director of the United States Patent and Trademark Office*